United States Patent
Haffner et al.

(10) Patent No.: US 9,173,775 B2
(45) Date of Patent: Nov. 3, 2015

(54) SYSTEM FOR DELIVERING MULTIPLE OCULAR IMPLANTS

(71) Applicant: Glaukos Corporation, Laguna Hills, CA (US)

(72) Inventors: David Steven Haffner, Mission Viejo, CA (US); Henrick K. Gille, Oceanside, CA (US); Charles Raymond Kalina, Jr., Irvine, CA (US); John Joseph Cogger, Santa Ana, CA (US)

(73) Assignee: GLAUKOS CORPORATION, Laguna Hills, CA (US)

(*) Notice: Subject to any disclaimer, the term of this patent is extended or adjusted under 35 U.S.C. 154(b) by 0 days.

(21) Appl. No.: 14/387,657

(22) PCT Filed: Mar. 14, 2013

(86) PCT No.: PCT/US2013/031636
§ 371 (c)(1),
(2) Date: Sep. 24, 2014

(87) PCT Pub. No.: WO2013/148275
PCT Pub. Date: Oct. 3, 2013

(65) Prior Publication Data
US 2015/0038893 A1 Feb. 5, 2015

Related U.S. Application Data

(60) Provisional application No. 61/615,479, filed on Mar. 26, 2012.

(51) Int. Cl.
*A61F 9/00* (2006.01)
*A61F 9/007* (2006.01)
*A61F 2/14* (2006.01)

(52) U.S. Cl.
CPC ............. *A61F 9/00781* (2013.01); *A61F 2/14* (2013.01); *A61F 9/0017* (2013.01); *A61F 2250/009* (2013.01)

(58) Field of Classification Search
USPC .................. 606/107, 108; 604/7, 8, 9, 10
See application file for complete search history.

(56) References Cited

U.S. PATENT DOCUMENTS

| 4,846,793 A | 7/1989 | Leonard et al. |
| 4,900,300 A | 2/1990 | Lee |

(Continued)

FOREIGN PATENT DOCUMENTS

| CA | 2643357 | 10/2008 |
| EP | 0436232 | 7/1991 |

(Continued)

*Primary Examiner* — Tuan V Nguyen
(74) *Attorney, Agent, or Firm* — Knobbe Martens Olson & Bear LLP

(57) ABSTRACT

Systems and methods for delivering multiple ocular implants to reduce intraocular pressure are disclosed. The ocular implants can be implanted at multiple sites within a single human eye without requiring removal of the delivery apparatus from the eye. A system for delivering multiple ocular implants can include at least two implants preloaded within a delivery device and configured to be implanted within the eye, a metering device configured to transfer energy to the implants for delivery at selected locations within the eye, wherein the metering device is configured to meter a variable amount of energy for each implant delivery event in the eye. The system can further include an injector mechanism configured to serially engage and drive each of the implants.

20 Claims, 22 Drawing Sheets

(56) References Cited

U.S. PATENT DOCUMENTS

| | | |
|---|---|---|
| 5,129,895 A | 7/1992 | Vassiliadis et al. |
| 5,290,295 A | 3/1994 | Querals et al. |
| 5,472,440 A | 12/1995 | Beckman |
| 5,558,637 A | 9/1996 | Allonen et al. |
| 5,681,323 A | 10/1997 | Arick |
| 5,833,694 A | 11/1998 | Poncet |
| 5,927,585 A | 7/1999 | Moorman et al. |
| 6,004,302 A | 12/1999 | Brierley |
| 6,045,557 A | 4/2000 | White et al. |
| 6,050,999 A | 4/2000 | Paraschac et al. |
| 6,071,286 A | 6/2000 | Mawad |
| 6,074,395 A | 6/2000 | Trott et al. |
| 6,146,387 A | 11/2000 | Trott et al. |
| 6,231,597 B1 | 5/2001 | Deem et al. |
| 6,450,984 B1 | 9/2002 | Lynch et al. |
| 6,464,724 B1 | 10/2002 | Lynch et al. |
| 6,524,275 B1 | 2/2003 | Lynch et al. |
| 6,544,249 B1 | 4/2003 | Yu et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,939,298 B2 | 9/2005 | Brown et al. |
| 6,955,656 B2 | 10/2005 | Bergheim et al. |
| 6,981,958 B1 | 1/2006 | Gharib et al. |
| 7,090,681 B2 | 8/2006 | Weber et al. |
| 7,094,225 B2 | 8/2006 | Tu et al. |
| 7,135,009 B2 | 11/2006 | Tu et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,431,710 B2 | 10/2008 | Tu et al. |
| 7,468,065 B2 | 12/2008 | Weber et al. |
| 7,488,303 B1 | 2/2009 | Haffner et al. |
| 7,563,241 B2 | 7/2009 | Tu et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,931,660 B2 * | 4/2011 | Aranyi et al. ................ 606/143 |
| 7,951,155 B2 | 5/2011 | Smedley et al. |
| 8,007,459 B2 | 8/2011 | Haffner et al. |
| D645,489 S | 9/2011 | Gille et al. |
| D645,490 S | 9/2011 | Gille et al. |
| 8,062,244 B2 | 11/2011 | Tu et al. |
| 8,070,290 B2 | 12/2011 | Gille et al. |
| 8,075,511 B2 | 12/2011 | Tu et al. |
| 8,152,752 B2 | 4/2012 | Lynch et al. |
| 8,333,742 B2 | 12/2012 | Bergheim et al. |
| 8,337,445 B2 | 12/2012 | Tu et al. |
| 8,388,568 B2 | 3/2013 | Lynch et al. |
| 8,506,515 B2 | 8/2013 | Burns et al. |
| 2002/0133168 A1 | 9/2002 | Smedley et al. |
| 2002/0143284 A1 | 10/2002 | Tu et al. |
| 2003/0055372 A1 | 3/2003 | Lynch et al. |
| 2003/0060752 A1 | 3/2003 | Bergheim et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0232015 A1 | 12/2003 | Brown et al. |
| 2003/0236484 A1 | 12/2003 | Lynch et al. |
| 2004/0024345 A1 | 2/2004 | Gharib et al. |
| 2004/0111050 A1 | 6/2004 | Smedley et al. |
| 2004/0147870 A1 | 7/2004 | Burns et al. |
| 2004/0154946 A1 | 8/2004 | Solovay et al. |
| 2004/0210185 A1 | 10/2004 | Tu et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0049578 A1 | 3/2005 | Tu et al. |
| 2005/0209549 A1 | 9/2005 | Bergheim et al. |
| 2005/0250788 A1 | 11/2005 | Tu et al. |
| 2005/0267478 A1 * | 12/2005 | Corradi et al. ................ 606/73 |
| 2005/0271704 A1 | 12/2005 | Tu et al. |
| 2005/0277864 A1 | 12/2005 | Haffner et al. |
| 2005/0288619 A1 | 12/2005 | Gharib et al. |
| 2006/0032507 A1 | 2/2006 | Tu |
| 2006/0074375 A1 | 4/2006 | Bergheim et al. |
| 2006/0084907 A1 | 4/2006 | Bergheim et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0241749 A1 | 10/2006 | Tu et al. |
| 2007/0088432 A1 | 4/2007 | Solovay et al. |
| 2007/0191863 A1 | 8/2007 | De Juan et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0045878 A1 | 2/2008 | Bergheim et al. |
| 2008/0228127 A1 | 9/2008 | Burns et al. |
| 2009/0076436 A2 | 3/2009 | Gharib et al. |
| 2009/0137983 A1 | 5/2009 | Bergheim et al. |
| 2009/0138081 A1 | 5/2009 | Bergheim et al. |
| 2010/0056979 A1 | 3/2010 | Smedley et al. |
| 2010/0185205 A1 | 7/2010 | Novakovic et al. |
| 2010/0234791 A1 | 9/2010 | Lynch et al. |
| 2011/0009874 A1 | 1/2011 | Wardle et al. |
| 2011/0009958 A1 | 1/2011 | Wardle et al. |
| 2011/0022065 A1 * | 1/2011 | Shipp ................ 606/151 |
| 2011/0092878 A1 | 4/2011 | Tu et al. |
| 2011/0105987 A1 | 5/2011 | Bergheim et al. |
| 2012/0071809 A1 | 3/2012 | Tu et al. |
| 2012/0078158 A1 | 3/2012 | Haffner et al. |
| 2012/0109040 A1 | 5/2012 | Smedley et al. |
| 2013/0018295 A1 | 1/2013 | Haffner et al. |
| 2013/0018296 A1 | 1/2013 | Bergheim et al. |
| 2013/0253528 A1 | 9/2013 | Haffner et al. |

FOREIGN PATENT DOCUMENTS

| | | |
|---|---|---|
| WO | WO 2008/061043 | 5/2008 |
| WO | WO 2009/097468 A2 | 8/2009 |
| WO | WO 2010/093945 | 8/2010 |
| WO | WO 2011/020633 A1 | 2/2011 |

* cited by examiner

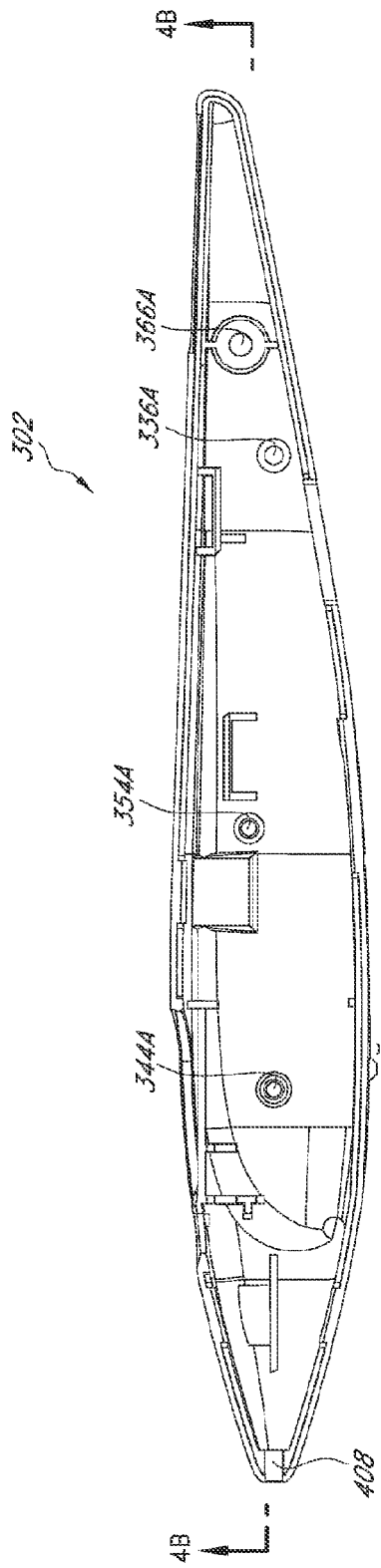
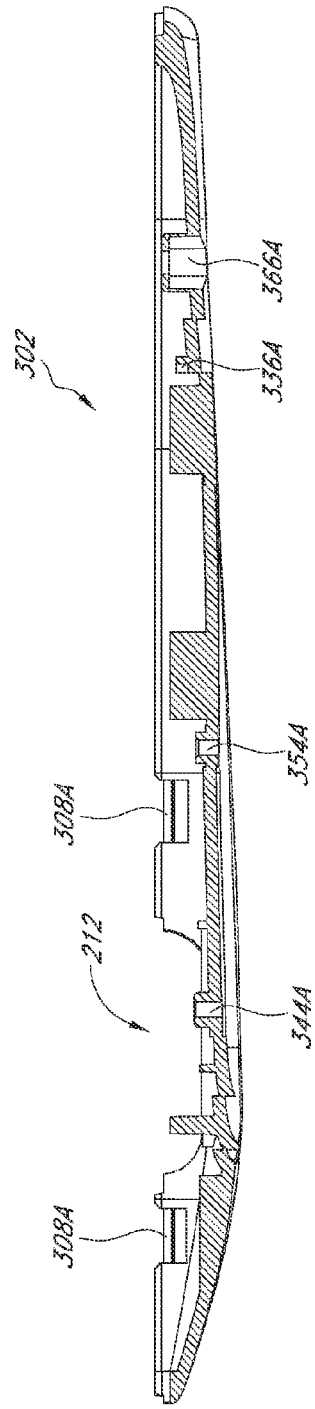
FIG. 4A
FIG. 4B

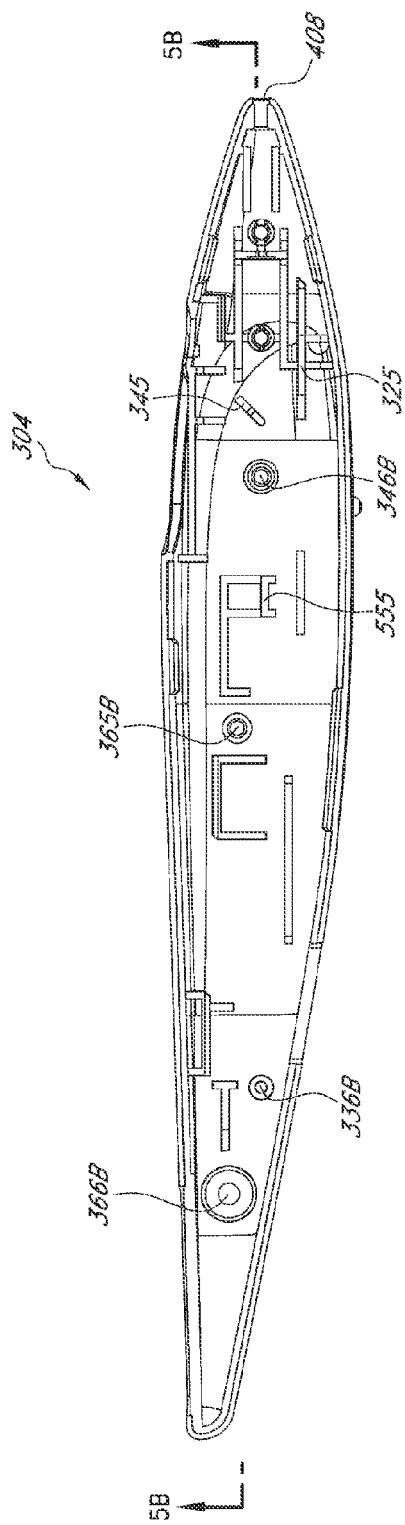
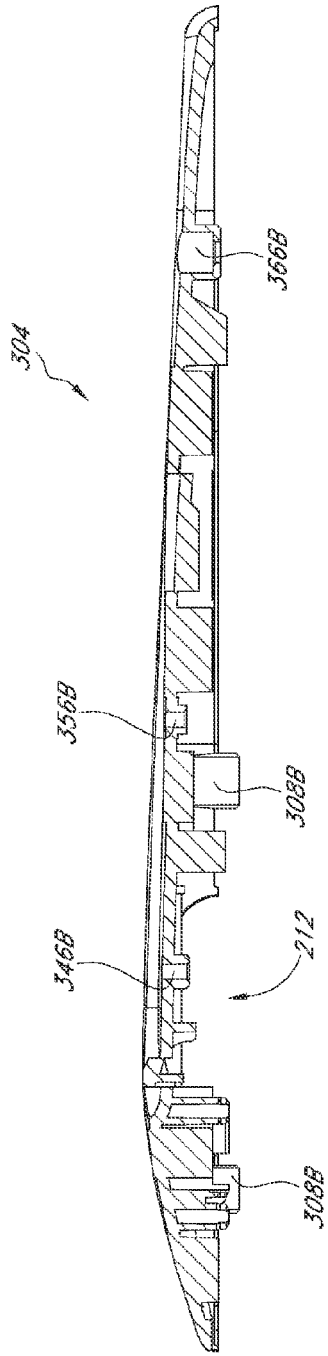
FIG. 5A
FIG. 5B

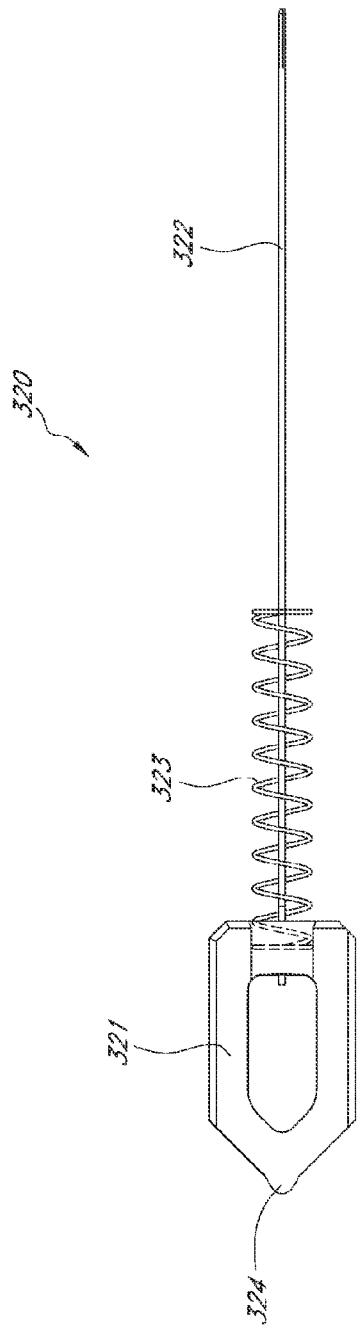
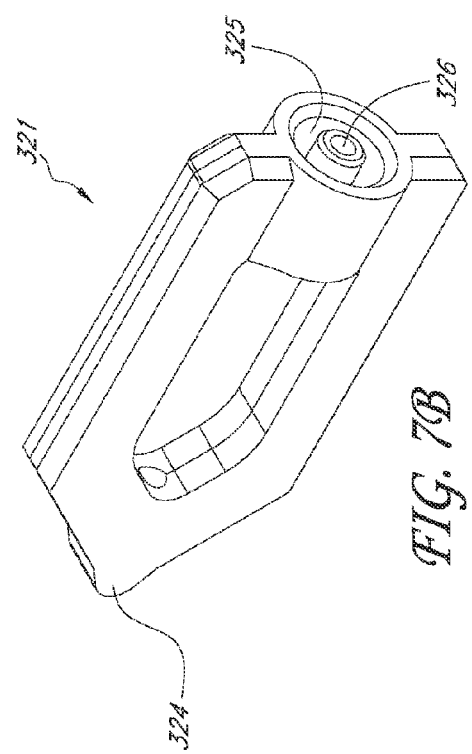
FIG. 7A
FIG. 7B

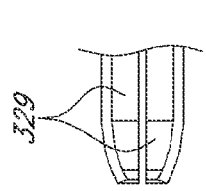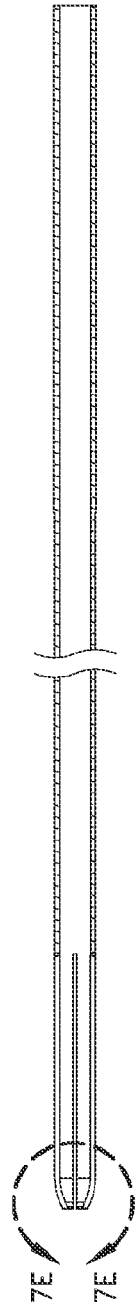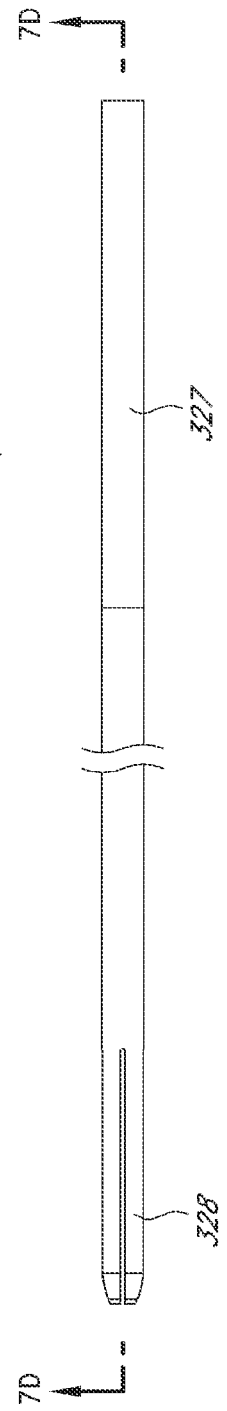
FIG. 7E
FIG. 7D
FIG. 7C

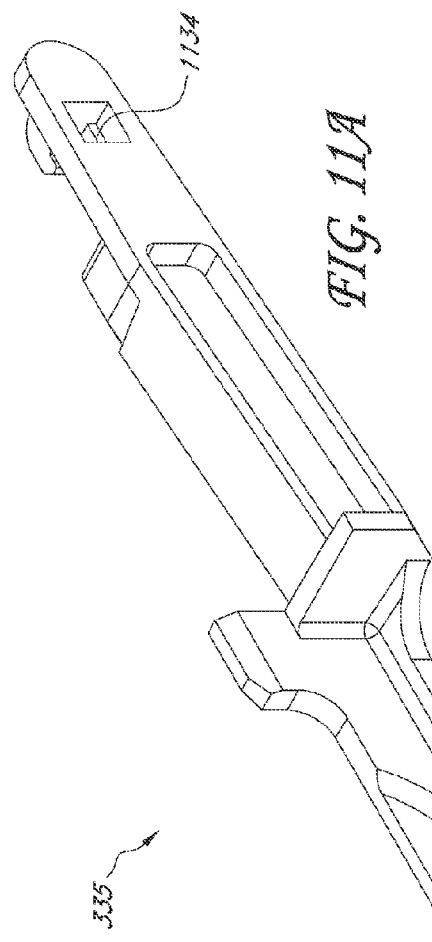
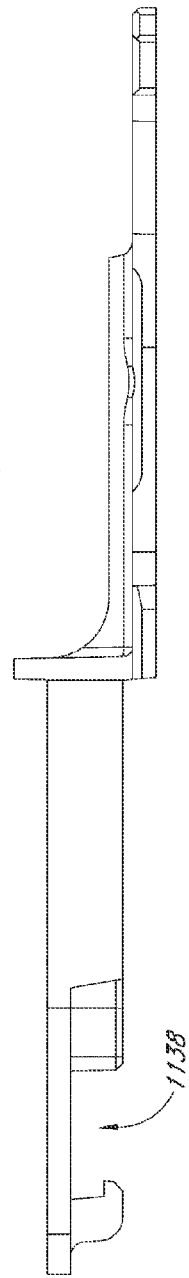
FIG. 11A
FIG. 11B

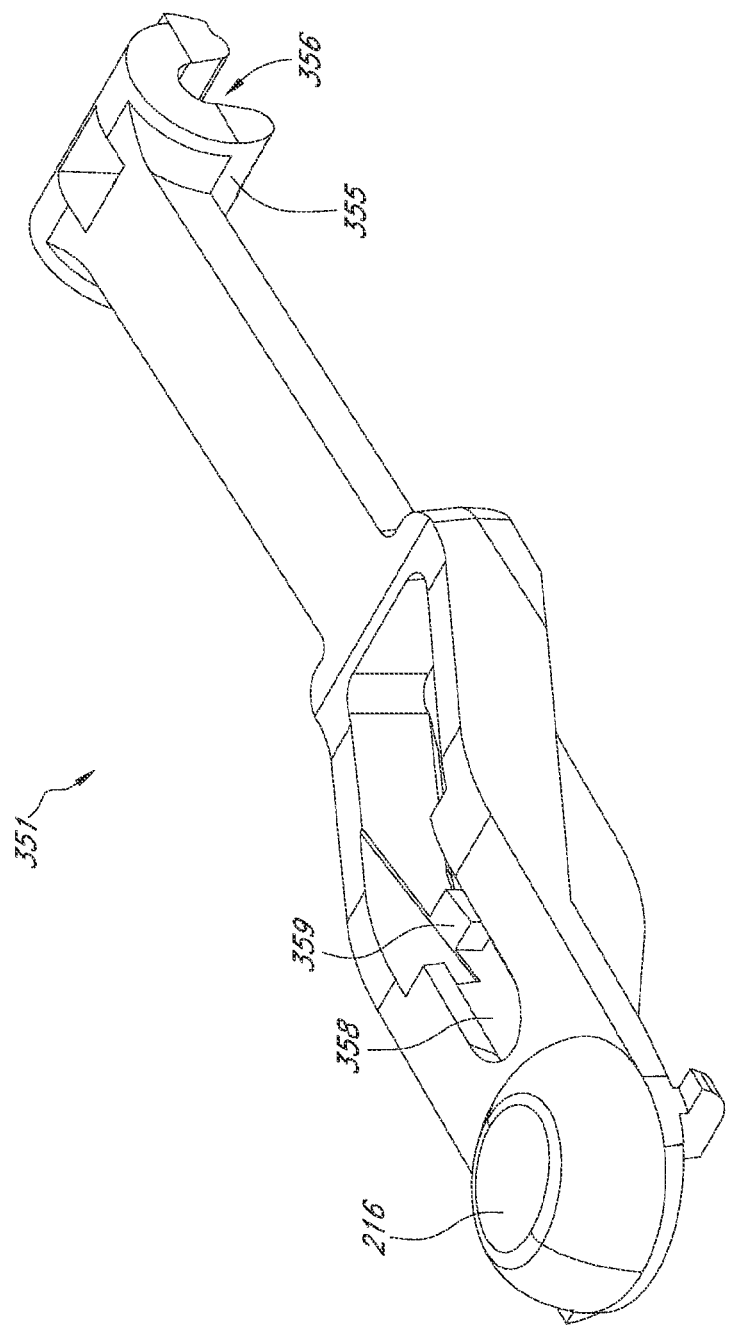

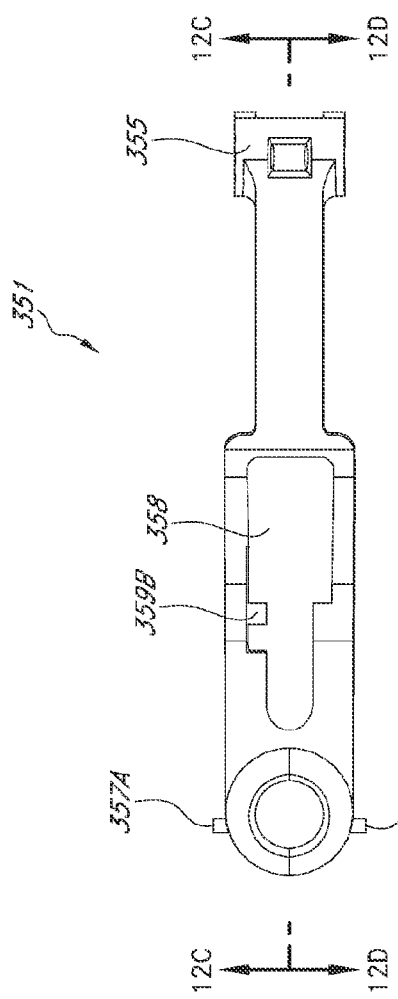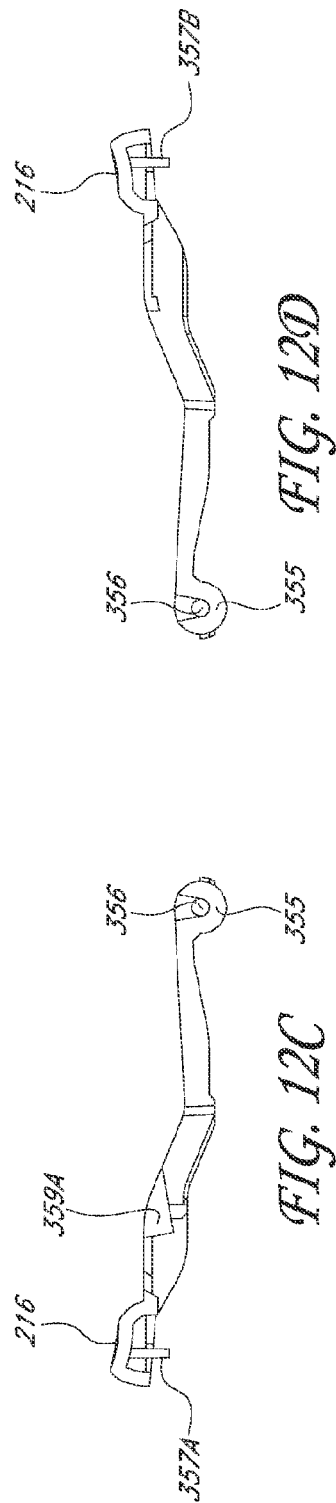

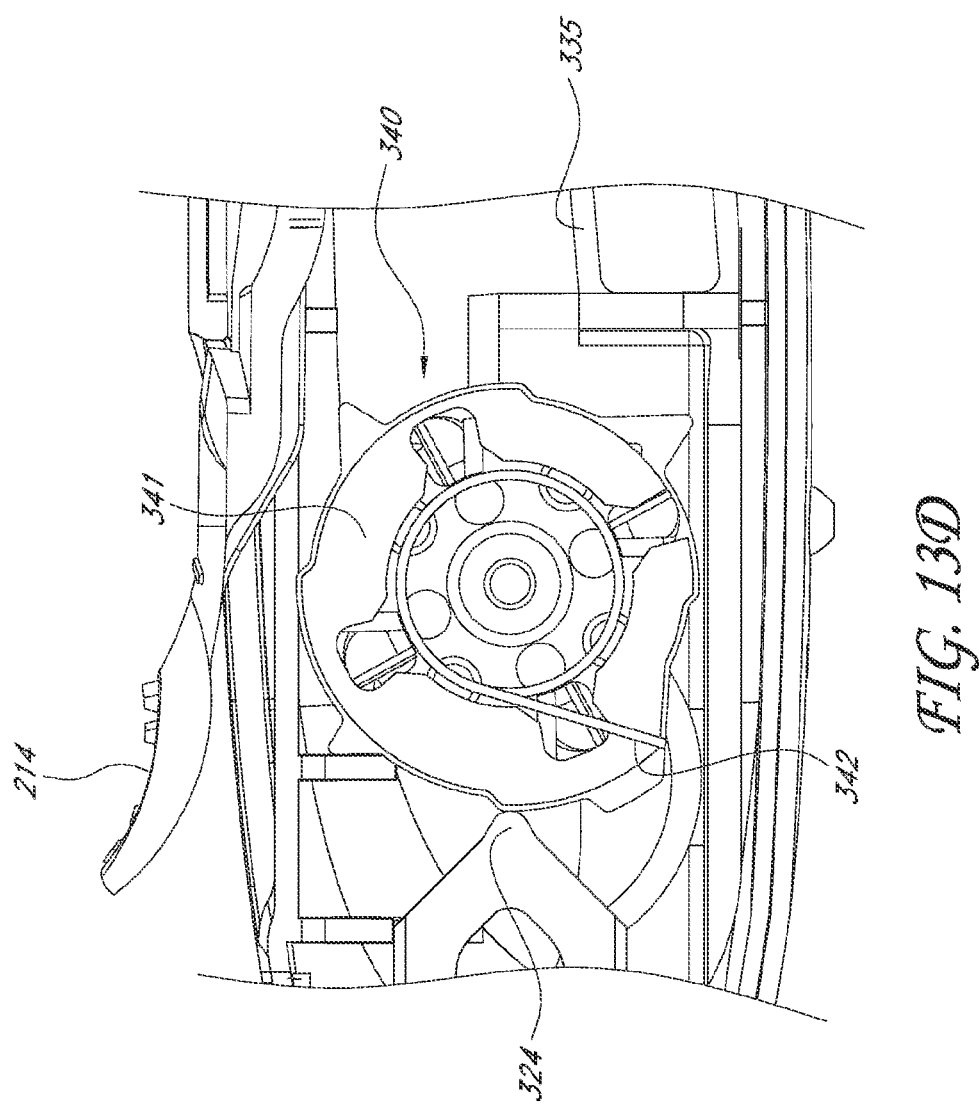

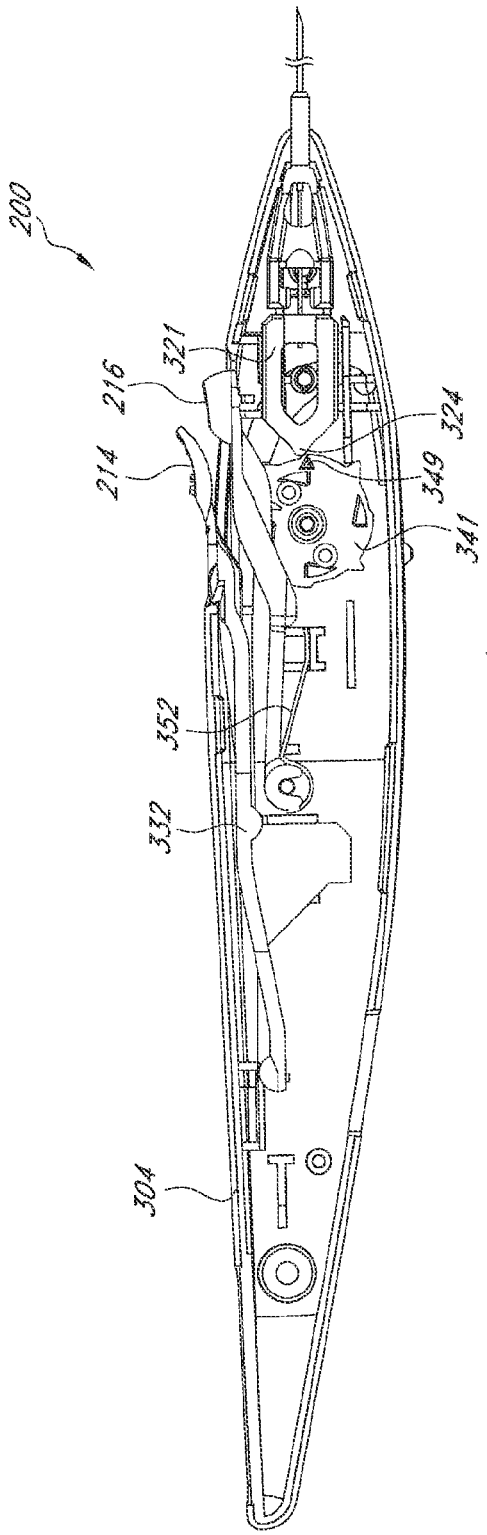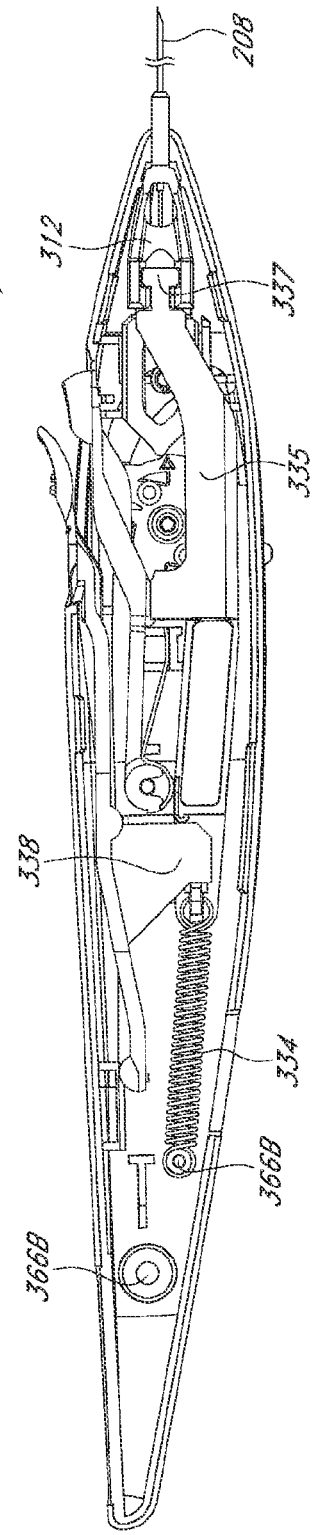

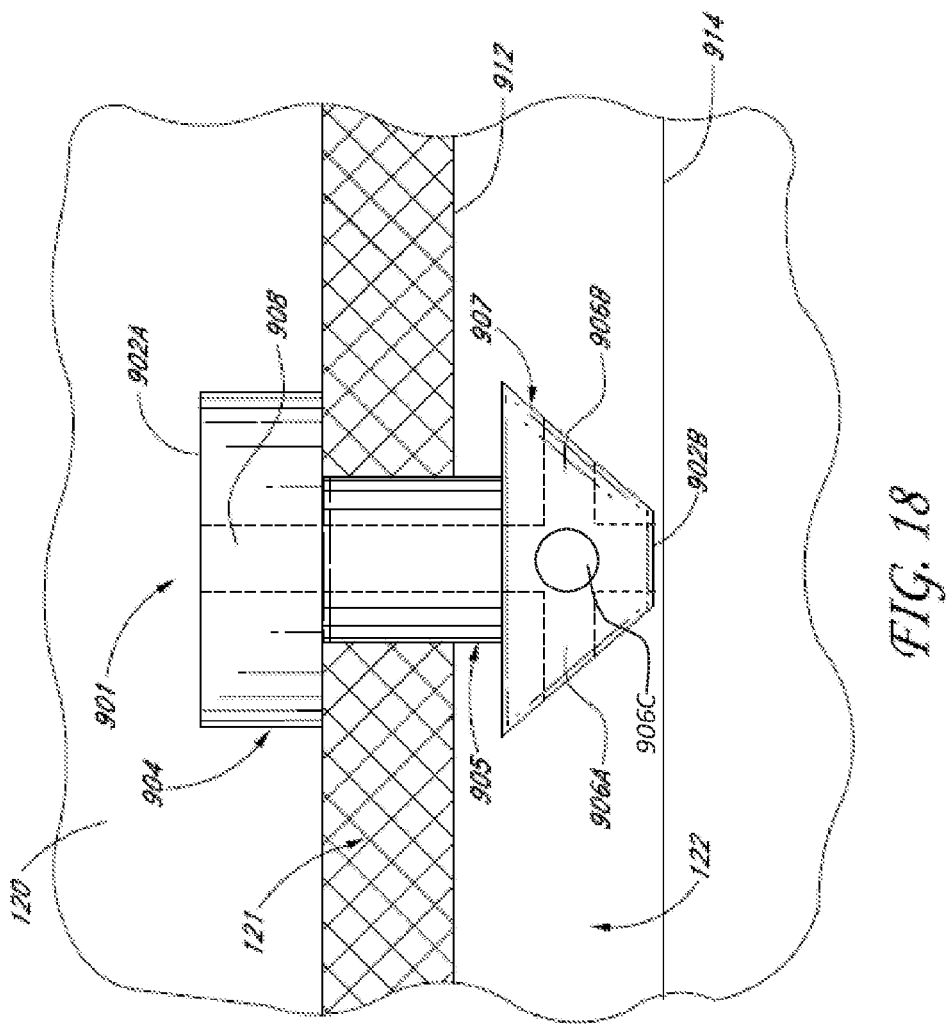

SYSTEM FOR DELIVERING MULTIPLE OCULAR IMPLANTS

RELATED APPLICATION

This application claims priority benefit of U.S. Provisional Application No. 61/615,479 filed Mar. 26, 2012, the entire contents of which are incorporated herein by reference.

FIELD

Embodiments of the inventions generally relate to intraocular pressure reduction and more specifically to systems, devices and methods for delivering multiple intraocular implants into the eye for treatment of ocular disorders.

BACKGROUND INFORMATION

A human eye is a specialized sensory organ capable of light reception and is able to receive visual images. Aqueous humor (hereinafter referred to as "aqueous") is a transparent liquid that fills at least the region between the cornea, at the front of the eye, and the lens. Aqueous is continuously secreted by ciliary processes of a ciliary body to the posterior chamber of the eye and the aqueous flows to the anterior chamber by crossing the pupil, so there is a constant flow of aqueous humor from the ciliary body to the anterior chamber of the eye. The aqueous fluid supplies nutrients to the avascular structures of the eye (for example, the cornea and the lens) and maintains intraocular pressure. Pressure within the eye is determined by a balance between the production of aqueous and its exit through canalicular outflow, uveoscleral outflow, or other outflow routes or pathways.

Many open-angle glaucomas are caused by an increase in the resistance to aqueous drainage through the trabecular meshwork and/or Schlemm's canal (e.g., the canalicular outflow pathways). The tissue of the trabecular meshwork normally allows the aqueous to enter Schlemm's canal, which then empties into aqueous collector channels in the posterior wall of Schlemm's canal and then into aqueous veins, which form the episcleral venous system. The uveoscleral outflow pathways can refer to the aqueous leaving the anterior chamber by diffusion through intercellular spaces among ciliary muscle fibers or through a supraciliary and/or suprachoroidal space.

Intraocular implants (for example, shunts or stents) can be implanted within the eye to facilitate the outflow of aqueous, thereby reducing intraocular pressure. Typical methods of implantation require relatively invasive surgical procedures, pose a risk of excessive trauma to the eye, and require excessive handling of the implant. For example, in a typical method of implantation, an incision is made through the sclera or cornea and the implant is inserted into the desired implantation location using forceps or another like manual grasping device. These forceps are configured for holding, and introducing into the eye only one implant at a time. This requires reloading and repositioning of the forceps prior to inserting each implant into the eye. Once the implants are deposited, the grasping device is removed and the incision is sutured closed.

Alternatively, a trocar, scalpel, or similar instrument can be used to pre-form an incision in the eye tissue before passing the implant into such tissue. After the incision is made in the eye tissue, a trocar can be advanced through the incision and then the implant can be delivered over the trocar.

Prior methods and systems for delivering multiple implants within the same eye typically require the delivery instrument to be removed from the eye and reloaded with a second implant. This reloading process increases the time of surgery, increases the risk of infection due to exposure and to excessive handling of the implant, and increases the risk of trauma to the eye due to multiple entries within an incision.

SUMMARY

A need exists for a more facile, convenient, less invasive, and less traumatic means of delivering multiple implants into the eye. In some embodiments of the present disclosure, a system and method for delivering multiple ocular implants at multiple implantation locations within internal eye tissue is provided that only requires a single incision within external eye tissue. In some aspects of the present disclosure, there is provided a system and method for delivering multiple ocular implants at a substantially constant speed and trajectory (e.g., velocity) at a specific controlled distance, thereby providing repeatability and consistency of deliveries within a single eye and of deliveries within multiple patients.

In accordance with some embodiments disclosed herein, a method of treating an ocular disorder is provided, comprising advancing an injector instrument loaded with multiple implants, sensors or other devices through an incision or opening in an eye and transmitting, transferring or otherwise delivering energy from an energy source to propel a first implant, previously loaded within or on the injector instrument, into eye tissue. The method also comprises repositioning the injector instrument and further transmitting or transferring energy from the energy source to propel a second implant, previously loaded within or on the injector instrument, into eye tissue at a second location spaced apart from the first location. The first and second implants are propelled at substantially the same speed, while the energy transmitted to propel the first implant out of the injector instrument to its implantation location is less than the energy transmitted to propel the second implant to its implantation location. In some embodiments, repositioning may be performed without removing the injector instrument from the eye. In some embodiments, the method comprises transmitting energy by unwinding or relaxing a torsion or non-torsion spring or by delivering energy from another stored energy or energy generation device (e.g., motor or electrical actuation device).

An injector instrument for treating an ocular disorder is disclosed in accordance with some embodiments disclosed herein. In some embodiments, the instrument comprises at least two implants loaded (e.g., pre-loaded) within or on the instrument. The instrument also comprises a source of energy for selectively releasing stored energy to deliver the implants into eye tissue and a cam operatively coupled to the source of energy that has a contoured profile configured to vary the amount of stored energy that is delivered to drive each implant out of the instrument to its implantation location. In some embodiments, the contoured profile of the cam may be the same for each implant delivery cycle. In some embodiments, the contoured profile of the cam may be different for each implant delivery cycle.

In accordance with some embodiments, a system for treating an ocular disorder comprises an injector instrument, or applicator, and at least two pre-loaded implants arranged in series and being configured to be implanted within eye tissue (to allow fluid flow therethrough). The instrument also comprises a metering device configured to transfer energy to the implants for delivery at selected locations of the eye tissue. The metering device can be configured to meter a variable amount of energy transferred for each implant delivery event in the eye tissue.

In accordance with some embodiments, an injector instrument for treating an ocular disorder comprises a trocar having a distal end configured to create openings in eye tissue. The instrument also comprises at least two implants loaded (e.g., pre-loaded) within the instrument. The implants comprise an inner lumen through which at least a portion of the trocar extends. The instrument further comprises a collet having a distal end spaced from the distal end of the trocar and having loaded therein at least some of the implants for delivery into eye tissue. The instrument also comprises an energy source operably coupled to the collet that is configured to release energy such that the distal end of the collet advances a respective one of the implants along the trocar and into the eye tissue, wherein the distance between the distal ends of the trocar and the collet can increase between each implant delivery cycle. In some embodiments, the distance between the distal ends of the trocar and the collet remain the same between each implant delivery cycle.

A delivery apparatus for implants is disclosed in accordance with some embodiments of the invention. The delivery apparatus comprises an incising member, multiple implants disposed in series along an axis of the incising member, and an injector mechanism configured to serially engage and drive each of the implants along the axis of the incising member. The incising member and the injector mechanism can, for example, be movable relative to each other from a first position, in which the incising member is positioned to cut eye tissue, to a second position, in which the incising member is moved proximally to inhibit the incising member from cutting.

A method for treating an ocular disorder is disclosed in accordance with some embodiments herein. In some embodiments, the method comprises providing an instrument having multiple implants preloaded thereon and advancing the instrument into an anterior chamber of an eye to locate a distal end of the instrument near a target implantation site. The method also comprises isolating a first implant and driving the isolated implant axially relative to the other implants using a driving member. The method further comprises implanting the first implant in eye tissue at the target implantation site using the driving member. The method also comprises implanting a second implant in eye tissue at another target implantation site.

BRIEF DESCRIPTION OF THE DRAWINGS

These and other features, aspects, and advantages of the present disclosure will now be described with reference to the drawings of embodiments of the invention, which embodiments are intended to illustrate and not to limit the scope of the disclosure.

FIG. 4A is a side view of the left housing illustrated in FIG. 3.

FIG. 4B is a longitudinal cross-section of the left housing of FIG. 4A.

FIG. 5A is a side view of the right housing illustrated in FIG. 3.

FIG. 5B is a longitudinal cross-section of the right housing of FIG. 5A.

FIG. 7A is a side view of the collet holder assembly of the multiple-implant delivery apparatus of FIG. 2, showing the collet holder, the collet return spring and the collet illustrated in FIG. 3.

FIG. 7B is an enlarged perspective view of the collet holder illustrated in FIG. 7A.

FIG. 7C is a side view of the collet illustrated in FIG. 7A.

FIG. 7D is a longitudinal cross-section of the collet of FIG. 7C.

FIG. 7E is an enlarged longitudinal cross-section of the fingered sleeve of the collet of FIG. 7D.

FIG. 11A is a perspective view of the needle retraction button link illustrated in FIG. 3.

FIG. 11B is a side view of the needle retraction button link of FIG. 11A.

FIG. 12A is a perspective view of the trigger button assembly illustrated in FIG. 3.

FIG. 12B is a top view of the trigger button assembly of FIG. 12A.

FIGS. 12C and 12D are longitudinal cross-section views of the trigger button assembly of FIG. 12B.

FIG. 13D is a partial cross-section of the cam assembly, showing a cam spring mounted on a cam, in accordance with an embodiment.

FIGS. 14A and 14B illustrate the assembly and interaction between the internal components of the multiple-implant delivery apparatus of FIG. 2.

FIG. 18 is an enlarged schematic and partial sectional view of Schlemm's canal and the trabecular meshwork of an eye illustrating the position and operation of an ocular implant delivered by the multiple-implant delivery apparatus of FIG. 2.

DETAILED DESCRIPTION

Embodiments of systems, devices and methods for delivering multiple ocular implants are described herein. In the following description, numerous specific details are set forth to provide a thorough understanding of the embodiments;

however, one skilled in the relevant art will recognize, based upon the disclosure herein, that the techniques described herein can be practiced without one or more of the specific details, or with other methods, components, materials, etc. In other instances, well-known structures, materials, or operations are not shown or described in detail to avoid obscuring certain aspects.

Reference throughout this description to "one embodiment" or "an embodiment" means that a particular feature, structure, or characteristic described in connection with the embodiment is included in at least one embodiment described herein. Thus, the appearances of the phrases "in one embodiment" or "in certain embodiments" in various places throughout this description are not necessarily all referring to the same embodiments. Furthermore, the particular features, structures, or characteristics may be combined in any suitable manner in one or more embodiments.

Figure 1A:
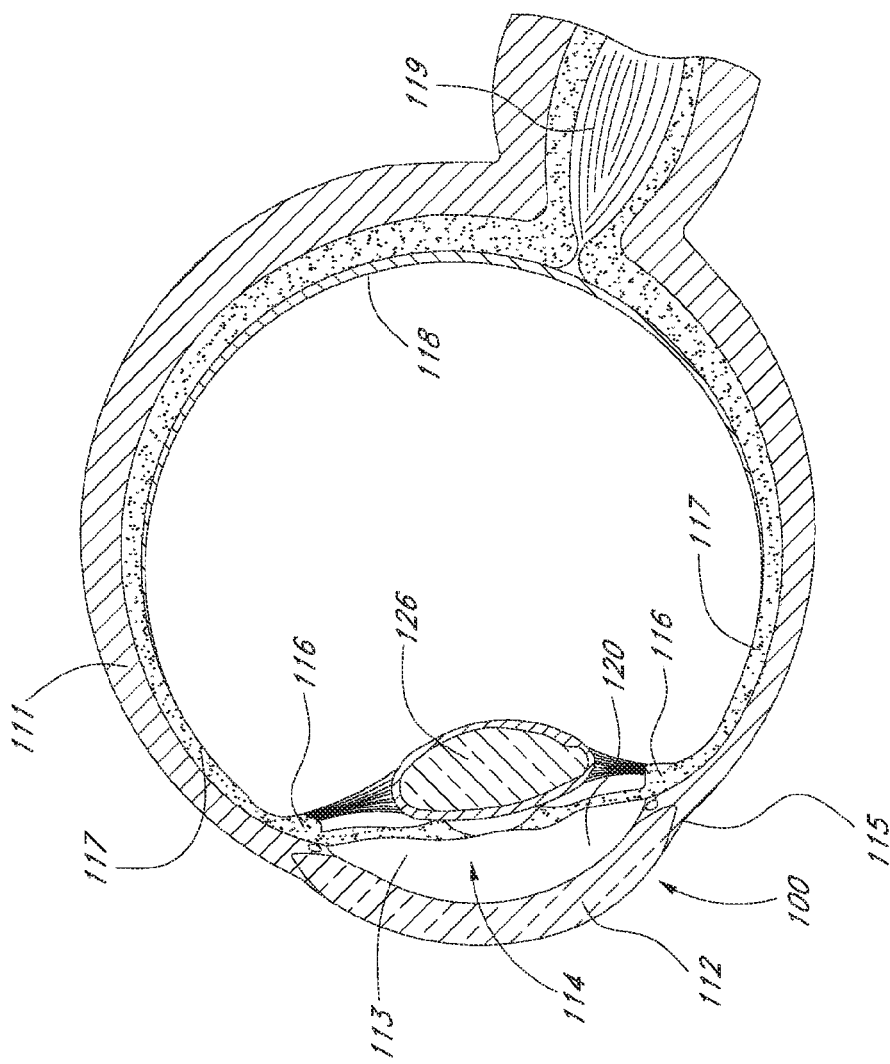
FIG. 1A is a schematic cross-sectional view of an eye.
Figure 1B:
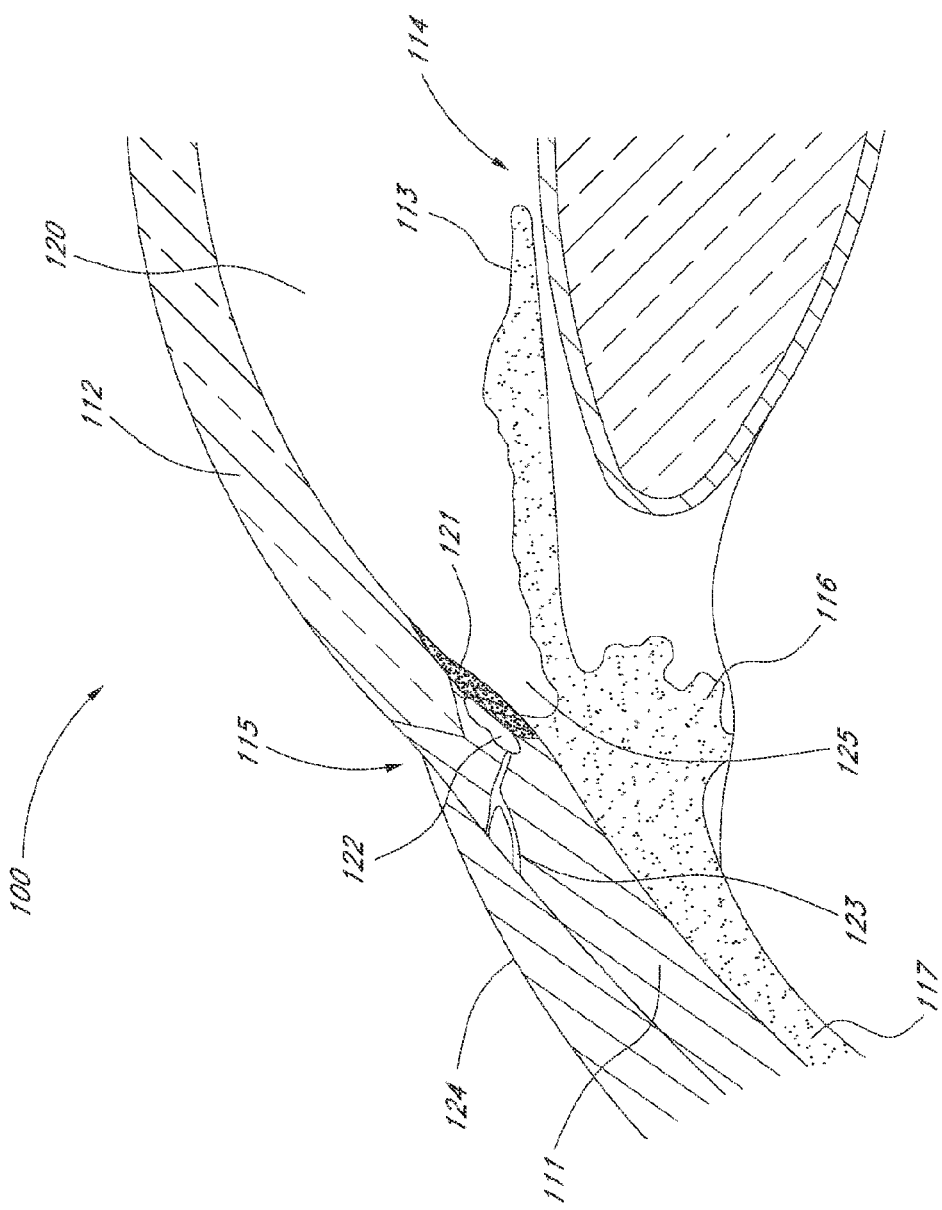
FIG. 1B is an enlarged cross-sectional view of an anterior chamber angle of the eye of FIG. 1A.

FIG. 1A is a cross-sectional view of an eye 100. FIG. 1B is an enlarged sectional view of the eye showing the relative anatomical locations of a trabecular meshwork 121, an anterior chamber 120, and Schlemm's canal 122. With reference to FIGS. 1A and 1B, the sclera 111 is a thick collagenous tissue that covers the entire eye 100 except a portion that is covered by a cornea 112. The cornea 112 is a thin transparent tissue that focuses and transmits light into the eye and through a pupil 114, which is a circular hole in the center of an iris 113 (colored portion of the eye). The cornea 112 merges into the sclera 111 at a juncture referred to as a limbus 115. A ciliary body 116 is vascular tissue that extends along the interior of the sclera 111 from the outer edges of the iris in the limbal region to a choroid 117. The ciliary body 116 is comprised of a ciliary processes and ciliary muscle. Ciliary zonules extend from the ciliary processes to a lens 126. The choroid 117 is a vascular layer of the eye 100, located between the sclera 111 and a retina 118. An optic nerve 119 transmits visual information to the brain and is the anatomic structure that is progressively destroyed by glaucoma.

With continued reference to FIGS. 1A and 1B, the anterior chamber 120 of the eye 100, which is bound anteriorly by the cornea 112 and posteriorly by the iris 113 and the lens 126, is filled with aqueous humor. Aqueous humor is produced primarily by the ciliary processes of the ciliary body 116 and flows into the posterior chamber, bounded posteriorly by the lens 126 and ciliary zonules and anteriorly by the iris 113. The aqueous humor then flows anteriorly through the pupil 114 and into the anterior chamber until it reaches an anterior chamber angle 125, formed between the iris 113 and the cornea 112.

As best illustrated by the drawing of FIG. 1B, in a normal eye, at least some of the aqueous humor drains from the anterior chamber 120 through the trabecular meshwork 121 via the canalicular route. Aqueous humor passes through the trabecular meshwork 121 into Schlemm's canal 122 and thereafter through a plurality of collector ducts and aqueous veins 123, which merge with blood-carrying veins, and into systemic venous circulation. Intraocular pressure is maintained by an intricate balance between secretion and outflow of aqueous humor in the manner described above. Glaucoma is, in most cases, characterized by an excessive buildup of aqueous humor in the anterior chamber 120, which leads to an increase in intraocular pressure. Fluids are relatively incompressible, and thus intraocular pressure is distributed relatively uniformly throughout the eye 100.

As shown in FIG. 1B, the trabecular meshwork 121 lies adjacent a small portion of the sclera 111. Exterior to the sclera 111 is a conjunctiva 124. Traditional procedures that create a hole or opening for implanting a device through the tissues of the conjunctiva 124 and sclera 111 involve extensive surgery, as compared to surgery for implanting a device, as described herein, which ultimately resides entirely within the confines of the sclera 111 and cornea 112.

In accordance with some embodiments, an ophthalmic implant system is provided that comprises multiple ocular implants and a delivery instrument for delivering and implanting the multiple ocular implants within eye tissue. These ocular implants can be configured to drain fluid from the anterior chamber of a human eye into a physiologic outflow pathway, such as Schlemm's canal, aqueous collector channels, episcleral veins, the uveoscleral outflow pathway, the supraciliary space, and/or the suprachoroidal space. The physiologic outflow pathway can be an existing space or outflow pathway (such as Schlemm's canal) or a potential space or outflow pathway (such as the suprachoroidal space). In some embodiments, the ocular implants are configured to be delivered to a location such that the implant communicates or allows fluid to communicate with an outflow pathway. While this and other systems and associated methods and apparatuses may be described herein in connection with glaucoma treatment, the disclosed systems, methods, and apparatuses can be used to treat other types of ocular disorders in addition to glaucoma or to implant other devices (such as pressure sensors or analyte sensors (e.g., glucose sensors)).

While a majority of the aqueous leaves the eye through the trabecular meshwork and Schlemm's canal, it is believed that a significant percentage of the aqueous in humans leaves through the uveoscleral pathway. The degree with which uveoscleral outflow contributes to the total outflow of the eye appears to be species dependent. As used herein, the term "uveoscleral outflow pathway" is to be given its ordinary and customary meaning to a person of ordinary skill in the art (and it is not to be limited to a special or customized meaning), and refers without limitation to the space or passageway whereby aqueous exits the eye by passing through the ciliary muscle bundles located angle of the anterior chamber and into the tissue planes between the choroid and the sclera, which extend posteriorly to the optic nerve. From these tissue planes, it is believed that the aqueous travels through the surrounding scleral tissue and drains via the scleral and conjunctival vessels, or is absorbed by the uveal blood vessels. It is unclear from studies whether the degree of physiologic uveoscleral outflow is pressure-dependent or pressure-independent.

As used herein, the term "supraciliary space" is to be given its ordinary and customary meaning to a person of ordinary skill in the art (and it is not to be limited to a special or customized meaning), and refers without limitation to the portion of the uveoscleral pathway through the ciliary muscle and between the ciliary body and the sclera, and the term "suprachoroidal space" is to be given its ordinary and customary meaning to a person of ordinary skill in the art (and it is not to be limited to a special or customized meaning), and refers without limitation to the portion of the uveoscleral pathway between the choroid and sclera.

The following description will include references to distal and proximal ends of various components and right and left sides of various components. The terms "distal" and "proximal" are to be given their ordinary and customary meaning to a person of ordinary skill in the art (and are not to be limited to a special or customized meaning), and refer without limitation to opposite regions or ends of a particular structure. In some embodiments, the term "distal" is used to refer to a region or end farther away from a person using the systems and devices described herein or performing the methods described herein and the term "proximal" is used to refer to a region or end closer to the person using the systems and devices described herein or performing the methods described herein; however, the meanings of the terms can be swapped.

The term "right side" should be understood to mean the side of the component that, upon assembly, faces the right housing of the multiple-implant delivery apparatus and the term "left side" should be understood to mean the side of the component that, upon assembly, faces the left housing of the multiple-implant delivery apparatus. However, these terms, as well as terms of orientation such as "top," "bottom," "upper," "lower," "front," "rear," and "end" are used herein to simplify the description of the context of the illustrated embodiments. Likewise, terms of sequence, such as "first" and "second," are used to simplify the description of the illustrated embodiments. Because other orientations and sequences are possible, however, the claims should not be limited to the illustrated orientations or sequences. Those skilled in the art will appreciate, upon reading this disclosure, that other orientations of the various components described above are possible.

Figure 2:
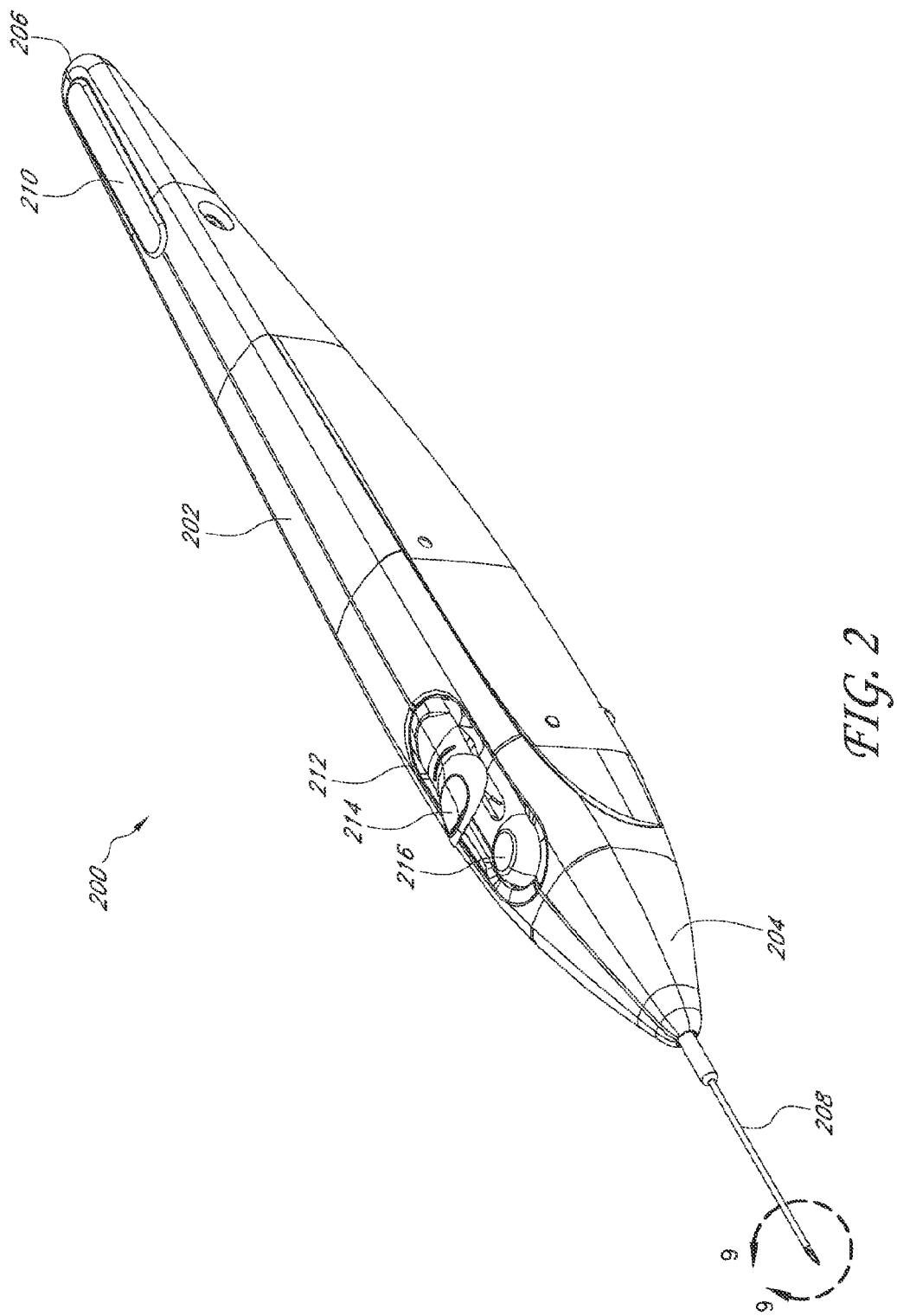
FIG. 2 is a perspective view illustrating an embodiment of a multiple-implant delivery apparatus.

FIGS. 2-13 illustrate a multiple-implant delivery apparatus, in accordance with embodiments of the invention. FIG. 2 is a perspective view illustrating external components of a multiple-implant delivery apparatus 200. As shown, the multiple-implant delivery apparatus 200 includes an external housing 202 comprising a distal end and a proximal end, with a main body extending therebetween. In the depicted embodiment, the distal end is gradually tapered to form a nose cone 204, from which extends a needle 208. As shown, the proximal end of the multiple-implant delivery apparatus 200 is also gradually tapered and can optionally include a label plate 210, which can be secured to the external housing 202, for example, by snapping, gluing, welding or other bonding methods. In certain embodiments, the label plate 210 is constructed of aluminum; however, it should be appreciated that the label plate 210 can be constructed of any rigid material (e.g. metal, plastic, or polymer). The label plate 210 can include, for example, a company or product name. External housing 202 further includes a button opening 212, out of which protrudes a needle retraction button 214 and a trigger button 216 for actuation by a user.

The multiple-implant delivery apparatus 200 is advantageously ergonomically shaped for easy gripping and manipulation, and has a general overall shape similar to a conventional writing instrument, such as a fountain pen. In one embodiment, the multiple-implant delivery apparatus 200 can be grasped by the user between the thumb and the middle finger, with the index finger free to press the needle retraction button 214 and the trigger button 216. In certain embodiments, tactile ridges (not shown) are provided on the external housing 202 in locations where the multiple-implant delivery apparatus 200 can be grasped to provide a more secure grip for the user.

Figure 3:
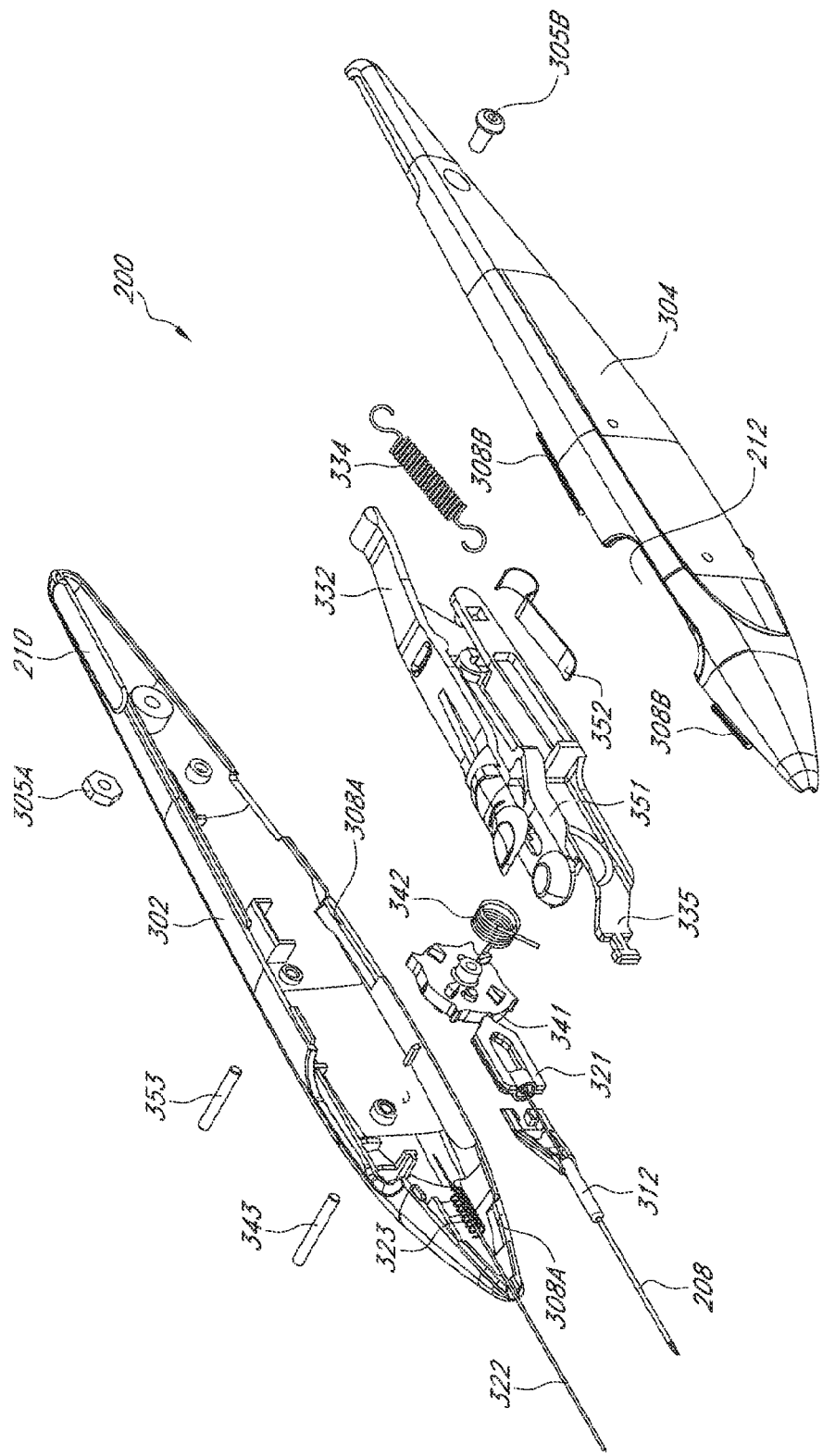
FIG. 3 is a perspective exploded view of the multiple-implant delivery apparatus of FIG. 2.

In certain embodiments, the external housing 202 is fabricated from a plurality of separate sections configured to be attached together. For example, the nose cone portion 204 and the tail portion 206 can be manufactured as separate pieces that are then secured to the main body of the external housing 202. In other embodiments, the external housing 202 is formed of two half-sections (as shown in FIG. 3).

As described further herein, multiple ocular implants can be pre-loaded into or onto the needle 208 and the multiple-implant delivery apparatus 200 can be used to deliver the multiple ocular implants at various desired locations within a mammalian (e.g., human) eye. For example, the needle 208 can be advanced through a preformed incision or opening in the eye. In another embodiment, the needle 208 can be advanced through external eye tissue (e.g., the cornea, limbus and/or sclera), creating an incision or opening through the eye as it is advanced into the eye tissue. As further described below, depression of the trigger button 216 actuates the multiple-implant delivery apparatus 200 and causes the ejection of a first implant into a desired first location within the patient's internal eye tissue. In one embodiment, the multiple-implant delivery apparatus 200 can then be repositioned without removing the needle 208 from the incision and a second implant can be delivered to a second location spaced apart from the first location. In another embodiment, the needle 208 can be removed from the incision and reinserted through eye tissue through a separate incision in order to deliver the second implant to the second implantation site. In accordance with several embodiments, the delivery of the multiple ocular implants advantageously is performed during an outpatient procedure without extensive surgery.

The combination of the overall external housing shape, together with the particular positioning of the needle retraction button 214 and the trigger button 216, allows the user to control the positioning of the needle 208 and to maintain its stability primarily through manipulation of the thumb and middle finger. The index finger meanwhile controls actuation of the multiple-implant delivery apparatus, and thus the ejection of the implants from the needle 208 at the multiple desired locations within the eye. This design effectively separates positioning control from actuation control, thereby reducing the risk that ejecting the implants will inadvertently cause movement of the multiple-implant delivery apparatus 200 such that the actual placement of an implant is not at the desired location.

Structure of Multiple-Implant Delivery Apparatus

FIG. 3 is an exploded perspective view of the multiple-implant delivery apparatus 200. The external components of the multiple-implant delivery apparatus 200 include a left housing 302, a right housing 304, a left fastener 305A, a right fastener 305B, and the label plate 210. As shown, the external housing 202 is formed of two separate half-sections (left housing 302 and right housing 304). When assembled, the proximal ends of left housing 302 and right housing 304 are held together by left fastener 305A and right fastener 305B. In the depicted embodiment, the left fastener 305A is a hexagonal shaped nut and the right fastener 305B is a hexagonal shaped socket screw; however, other shapes and types of fasteners can be used as desired and/or required. The middle and distal ends of the left housing 302 and the right housing 304 can, in one embodiment, be configured to snap together via snap-fit members 308A, 308B disposed on each of left housing 302 and right housing 304. Although the depicted embodiment shows fasteners 305A, 305B and snap-fit members 308A, 308B, other methods of fastening the two half-sections together are contemplated, including, for example, gluing, welding, fusing, Velcro, and adhesive bonding. In addition, in alternative embodiments, the external housing 202 could be separated into top and bottom half-sections instead of right and left half-sections. In yet other alternative embodiments, the external housing 202 is formed of more than two sections configured to be attached together to form a contiguous unit.

With continued reference to FIG. 3, the internal components of the multiple-implant delivery apparatus 200 include a needle assembly (including a needle holder 312 and the needle 208); a collet holder assembly 320 (including a collet holder 321, a collet 322, and a collet return spring 323); a trocar assembly 800 (shown in FIG. 8); a needle retraction assembly (including a needle retraction button unit 332, a needle retraction spring 334, and a needle retraction link 335); a cam assembly (including a cam 341, a cam spring 342, and a cam dowel pin 343); and a trigger button assembly (including a trigger unit 351, a trigger spring 352, and a trigger dowel pin 353).

The internal components can be secured to or within the right housing 304 during assembly of the multiple-implant delivery apparatus 200 using various methods of fixation (e.g., adhesion, bonding, gluing, snap-fitting, and the like). The interaction of the internal components and the operation of the multiple-implant delivery apparatus will be discussed in more detail later in connection with FIGS. 14-16.

In certain embodiments, the multiple-implant delivery apparatus 200 is disposable and includes one or more safety mechanisms that prevent reuse. For example, the safety mechanism can be an internal component that renders the instrument inoperable if re-sterilized. For example, the safety mechanism can prevent reloading of implants, can prevent retraction of the needle after use, and/or can prevent the assembly that provides the energy to deliver the implants from being reused. In other embodiments, the multiple-implant delivery apparatus 200 can be reloaded with implants, sterilized, and re-used on the same or a different patient.

FIGS. 4A and 4B illustrate the left housing 302 in more detail. FIG. 4A is a side view of the interior of the left housing 302 and FIG. 4B is a longitudinal cross-section of FIG. 4A. The left housing 302 includes features for attachment to the right housing 304 and features for receiving the internal components of the multiple-implant delivery apparatus 200. The attachment features include a left fastener slot 366A and snap-fit members 308A. The left fastener slot 366A is sized and shaped to receive the left fastener 305A, which in the illustrated embodiment of the multiple-implant delivery apparatus 200 of FIG. 2 is a hexagonal-shaped nut. The left fastener slot 366A is recessed within the left housing 302 so that the left fastener 305A does not extend out beyond the exterior surface of the left housing 302 upon assembly and so that the left fastener 305A remains securely in place. The snap-fit members 308A of the left housing 302 include slots that are configured to receive and engage with tabs of corresponding snap-fit members 308B of the right housing 304.

The receiving, or mounting, features of the left housing 302 include a left needle retraction spring mount 336A, a left cam mount 344A, a left trigger unit mount 354A, the left half of a needle opening 408, and the left half of the button opening 212. The receiving features will be discussed in more detail in connection with the description of corresponding receiving features of the right housing 304.

FIGS. 5A and 5B illustrate the right housing 304 in more detail. The right housing 304 includes attachment and receiving features corresponding to those described in connection with the left housing 302. For example, the attachment features of the left housing include a right fastener slot 366B and snap-fit members 308B. The right fastener slot 366B is configured to receive the right fastener 305B. In the depicted embodiment, the right fastener slot 366B is circular in order to receive the right fastener 305B, which in the depicted embodiment, is a screw with a circular head. The right fastener slot 366B is recessed within the right housing 304 so that the right fastener 305B does not extend out beyond the surface of the right housing 304 upon assembly and so that the right fastener 305B remains securely in place during delivery and use. The snap-fit members 308B include ridged tabs that are configured to snap into the slots of snap-fit members 308A of the left housing 302. In certain embodiments, there is an audible click when snap-fit members 308A and snap-fit members 308B are fully engaged.

The corresponding receiving, or mounting, features include a right needle retraction spring mount 336B, a right cam mount 346B, a right trigger unit mount 356B, the right half of the needle opening 408, and the right half of the button opening 212. The right needle retraction spring mount 336B is configured to align with the left needle retraction spring mount 336A and together, the right and left needle retraction spring mounts 336 are sized and configured to receive and fixedly secure one end of the needle retraction spring 334. The right cam mount 346B is configured to align with the left cam mount 346A and together, the right and left cam mounts 346 are sized and configured to receive the cam dowel pin 343, which provides a mount and rotational pivot for the cam 341. The right trigger unit mount 356B is configured to align with the left trigger unit mount 356A and together, the right and left trigger unit mounts 356 are sized and configured to receive the trigger dowel pin 353, which provides a mount and pivot for the trigger unit 351.

The right housing 304 additionally includes various engagement members. The engagement members can include protrusions from the inner wall of the right housing 304 that engage portions of various internal components of the multiple-implant delivery apparatus 200. For example, engagement member 555 engages the distal end of the trigger spring 352, engagement member 345 engages one end of the cam spring 342, and engagement member 325 engages the collet holder 321.

In certain embodiments, the left housing 302 and the right housing 304 can be composed of any rigid or semi-rigid material, such as plastic, polymer, metal, composites, or the like. In certain embodiments, the left housing 302 and the right housing 304 are molded from Lexan® polycarbonate. In other embodiments, at least a portion of the left housing 302 and/or the right housing 304 can be composed of a flexible material, such as silicone or similar elastomeric or flexible polymers.

Figures 6A, 6B:
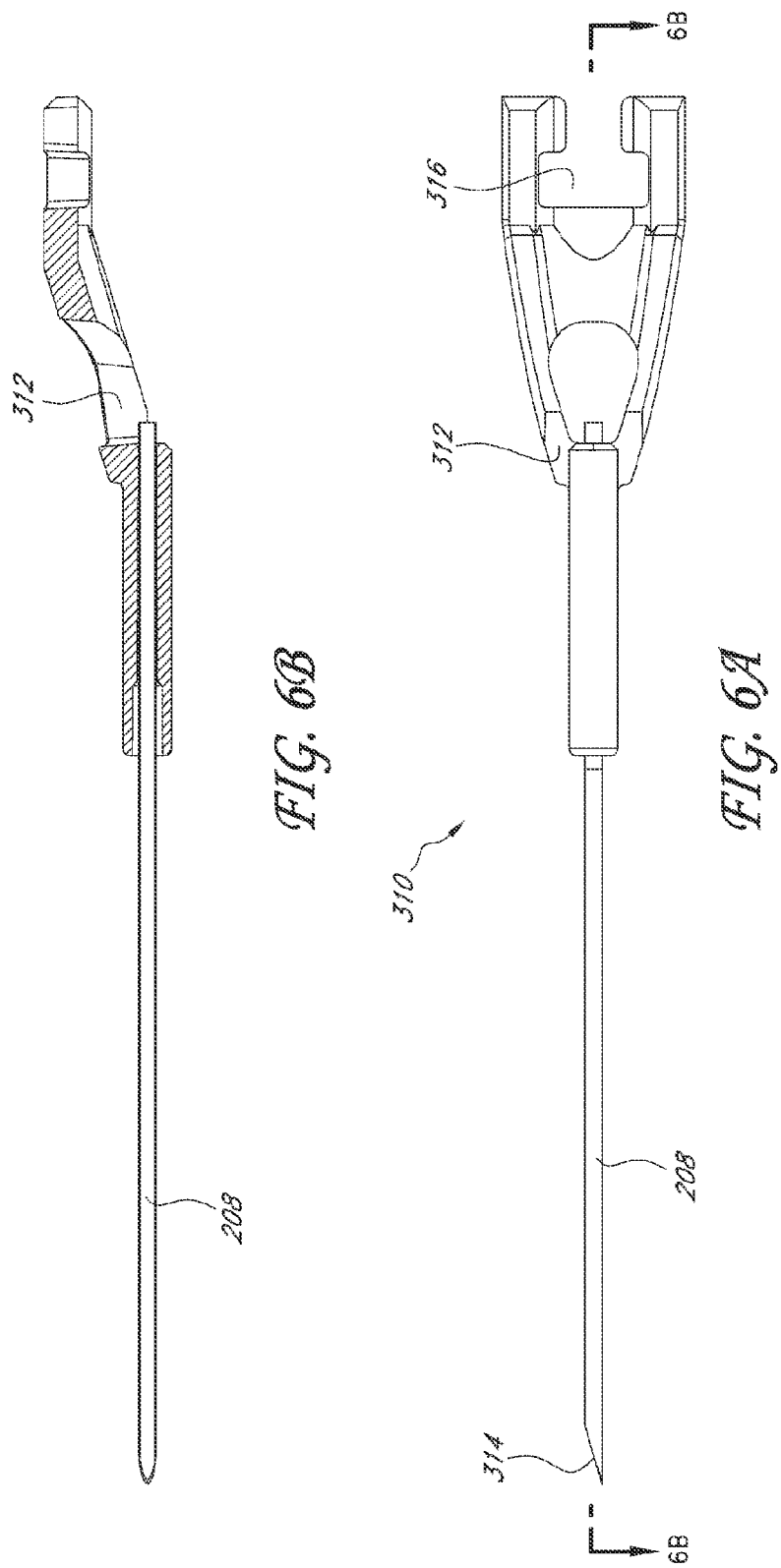
FIG. 6A is a side view of the needle assembly illustrated in FIG. 3.
FIG. 6B is a longitudinal cross-section of the needle assembly of FIG. 6A.

FIGS. 6A and 6B illustrate an embodiment of a needle assembly 310 to be utilized with the multiple-implant delivery apparatus 200. FIG. 6A is a side view of the right side of the needle assembly 310. FIG. 6B is a longitudinal cross-section of FIG. 6A. The needle assembly 310 includes the needle 208 and the needle holder 312. In certain embodiments, upon assembly, the needle 208 is bonded to the needle holder 312 using an ultraviolet ("UV") light-curing or other type of adhesive or bonding method; however, other attachment (e.g., bonding, welding, clamping, press-fitting) methods are contemplated.

In certain embodiments, the needle 208 is constructed of stainless steel and includes a needle tip 314 having a beveled, tapered, or otherwise sharpened edge oriented as shown in FIG. 6A. The beveled edge can be formed at a standard 15-degree angle or other angles as desired and/or required. In certain embodiments, the needle 208 advantageously includes a tri-beveled edge for less traumatic insertion. The needle 208 can have a small diameter size so that the incision is self-sealing without suturing upon withdrawal of the needle 208 from the eye. In certain embodiments, an outer diameter of the needle 208 is preferably no greater than about 18-gauge and not smaller than about 27-gauge. In certain embodiments, the needle 208 can advantageously be a hollow 23-gauge needle with an outer diameter of about 0.025 inches and an inner diameter of about 0.0205 inches. However, the needle 208 can have other suitable dimensions. In certain embodiments, the needle 208 advantageously has a low-friction or lubricious coating on at least a portion of the needle 208. In certain embodiments, the needle 208 advantageously has a hydrophobic coating, a hydrophilic coating, a hydrophilic coating, and/or other low-friction coating on at least a portion of the needle 208. In certain embodiments, the coating is applied to the outside surfaces of the needle 208 (including the cutting features) but not on the inside surfaces. In some embodiments, the needle 208 is replaced with any suitable piercing member configured to create an incision in external eye tissue, such as a cannula, a scalpel and the like.

Besides holding the needle 208 in place, the needle holder 312 interfaces with the needle retraction link 335 to facilitate needle retraction. The needle holder 312 includes a needle retraction link slot 316 sized and shaped to match the profile of the distal end of the needle retraction link 335. The needle holder 312 is formed of any rigid material, such as a plastic or polymer. In certain embodiments, the needle holder 312 is molded from VECTRA® liquid crystal polymer ("LCP") manufactured by Ticona; however, other polymeric materials can be used as desired (for example, neoprene, nylon, polyvinyl chloride (PVC), polystyrene, polyethylene, polypropylene, polyacrylonitrile, silicone, polyvinyl butyral (PVB), acrylonitrile butadiene styrene (ABS)). The needle holder 312 extends from the needle 208 at an angle that is offset from the longitudinal axis of the needle 208.

FIG. 7A is a side view of an embodiment of a collet holder assembly 320 of the implant delivery device 200. As shown, the collet holder assembly 320 includes the collet holder 321, the collet 322, and the collet return spring 323. In certain embodiments, upon assembly, the collet 322 is bonded to the collet holder 321 using a UV light curing or other type of adhesive method; however, other bonding methods are contemplated (for example, bonding, welding, other adhesives, press-fitting). The collet return spring 323 is loaded onto the collet 322 during assembly. The collet return spring 323 can be a coil or helical spring (e.g., tension/extension or compression spring) constructed of stainless steel wire; however, metals other than stainless steel or polymeric materials can also be used as desired). In certain embodiments, the collet return spring 323 can advantageously be formed of coiled stainless steel wire having about a 0.006-inch wire diameter and a free length of about 0.5 inches and a spring diameter of about 0.08 inches; however, the collet return spring 323 can have other suitable dimensions as desired and/or required without limitation. In operation, the collet return spring 323 provides a bias force to the collet holder 321 that maintains engagement between the collet holder 321 and the contoured surface of the cam 341. It should be appreciated that the collet return spring 323 can be replaced with any suitable mechanism for providing a bias force (for example, a torsion spring, a leaf spring, a non-torsion spring such as a compression spring, a flat spring, a hairspring, a balance spring, a V-spring, a volute spring, an elastomeric band, magnetic coupling, gas compression).

FIG. 7B is an enlarged perspective view of the collet holder 321. The collet holder 321 includes a cam follower 324 that engages and follows the contoured surface profile of the cam 341. The collet holder 321 further includes an outer bore 325 sized and shaped for receiving an end of the collet return spring 323 and an inner bore 326 sized and shaped for receiving an end of the collet 322. In certain embodiments, the outer bore 325 has a diameter of about 0.09 inches and the inner bore 326 has a diameter of about 0.026 inches; however, other suitable dimensions are contemplated (for example, the outer bore 325 can have a diameter between about 0.01 inches and about 0.20 inches and the inner bore 326 can have a diameter of about 0.001 inches and about 0.10 inches). The collet holder 321 is molded from Vectra® LCP manufactured by Ticona in certain embodiments; however, other polymeric materials can be used as desired (for example, neoprene, nylon, polyvinyl chloride (PVC), polystyrene, polyethylene, polypropylene, polyacrylonitrile, silicone, polyvinyl butyral (PVB), acrylonitrile butadiene styrene (ABS)).

FIGS. 7C-7E illustrate the structural details of the collet 322. The collet 322 can be a solid body 327 with a slotted sleeve 328. The slotted sleeve 328 can have four fingers 329 bounded by four slits spaced 90 degrees apart from each other and having a length from about 0.05 inches to 0.25 inches; however, in other embodiments, the slotted sleeve 328 can have more or fewer fingers disposed at other angular spacings. In certain embodiments, the collet 322 is advantageously constructed of Nitinol (nickel titanium alloy) material; however, the collet 322 can be constructed of any suitable flexible material (for example, flexible metal or polymer). The slotted sleeve 328 can further include a beveled, or chamfered, edge to improve lateral movement of the collet 322 during operation of the multiple-implant delivery apparatus 200.

Figure 8:
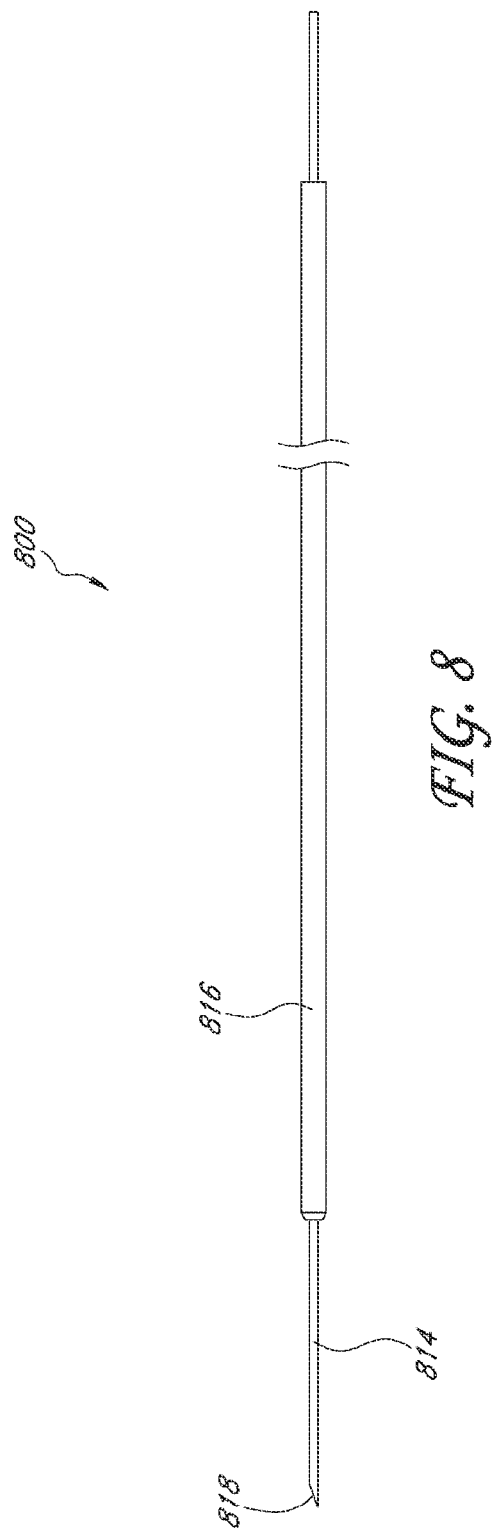
FIG. 8 is a side view illustrating an embodiment of a trocar assembly to be used in the multiple-implant delivery apparatus of FIG. 2.

FIG. 8 is a side view illustrating an embodiment of a trocar assembly 800 of the multiple-implant delivery apparatus 200 to deliver multiple ocular implants. The trocar assembly 800 includes a trocar 814 and a backup tube 816. As shown, the cutting tip 818 can be beveled, tapered, and/or sharpened to facilitate insertion. The cutting tip 818 can form an implantation opening, or channel, in internal eye tissue (e.g. trabecular meshwork) into which an implant can be delivered. In one embodiment, the diameter of the trocar 814 is about 0.003 inches and the length is about 2.3 inches. In other embodiments, the diameter of the trocar 814 can be from about 0.001 inches to 0.01 inches and the length can be any suitable length to enable loading and delivery of multiple implants (for example, 0.5 inch to 5 inches).

The backup tube 816 includes a hollow tube having an inner diameter sized to receive the trocar 814. In certain embodiments, backup tube 816 has an inner diameter of about 0.0035 inches; however, the backup tube 816 can have any inner diameter sized so as to receive the trocar 814. As shown, the backup tube 816 can include a chamfered distal end 819. In certain embodiments, the backup tube 816 is advantageously laser welded to the trocar 814 upon assembly. In other embodiments, the backup tube 816 can be bonded to the trocar 814 using other methods of fixation (for example, curing, welding, press-fitting, adhesive).

The trocar 814 can be angled or curved in certain embodiments. The trocar 814 can be rigid, semi-rigid, or flexible. In certain embodiments, some portions of the trocar 814 are flexible and other portions are rigid. In embodiments where the trocar 814 can be stiff, the implant can be, but need not be relatively flexible. In certain embodiments, the trocar 814 and the backup tube 816 are advantageously constructed of stainless steel. In other embodiments, the trocar 814 and the backup tube 816 can be constructed of other suitable materials, such as other metals, plastics, or polymers.

Figure 9:
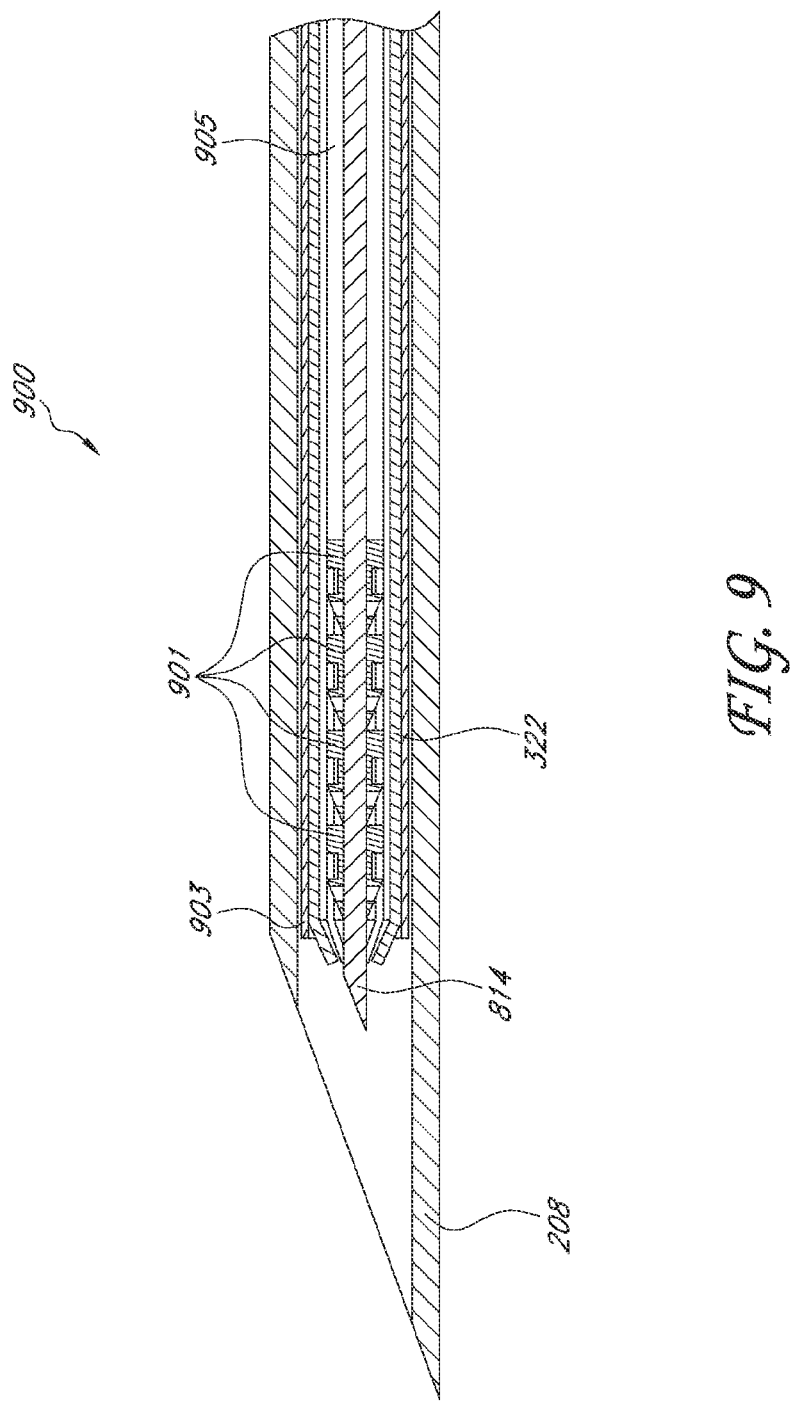
FIG. 9 is a longitudinal cross-section of the needle end of the multiple-implant delivery apparatus of FIG. 2, showing multiple ocular implants ready for delivery.

FIG. 9 illustrates a longitudinal cross-section of the needle end 900 of the multiple-implant delivery apparatus 200. As shown, four ocular implants 901 have been pre-loaded onto the trocar 814 during assembly. However, the multiple-implant delivery apparatus 200 can receive more or fewer than four implants for implantation into internal eye tissue. In certain embodiments, the ocular implants are disposed in series along a longitudinal axis of the trocar 814 (e.g., arranged in tandem). In various embodiments, upon assembly, the trocar 814 is retained within the collet 322. In some embodiments, the trocar 814 can move longitudinally within the collet 322. In other embodiments, the trocar 814 is fixed relative to the collet 322. In various embodiments, upon assembly, the collet 322 is housed within an insertion tube 903, which can be fixed relative to the trocar 814. The insertion tube 903 can advantageously comprise a hollow hypodermic tube constructed of stainless steel. In alternative embodiments, the insertion tube 903 can be constructed of any rigid material, such as metal, plastic, or polymer. The internal diameter of the insertion tube 903 can range from about 0.005 inches to about 0.080 inches, from about 0.010 inches to about 0.030 inches, from about 0.015 inches to about 0.020 inches, from about 0.005 inches to about 0.040 inches, from about 0.020 inches to about 0.060 inches, or overlapping ranges thereof.

Figure 10:
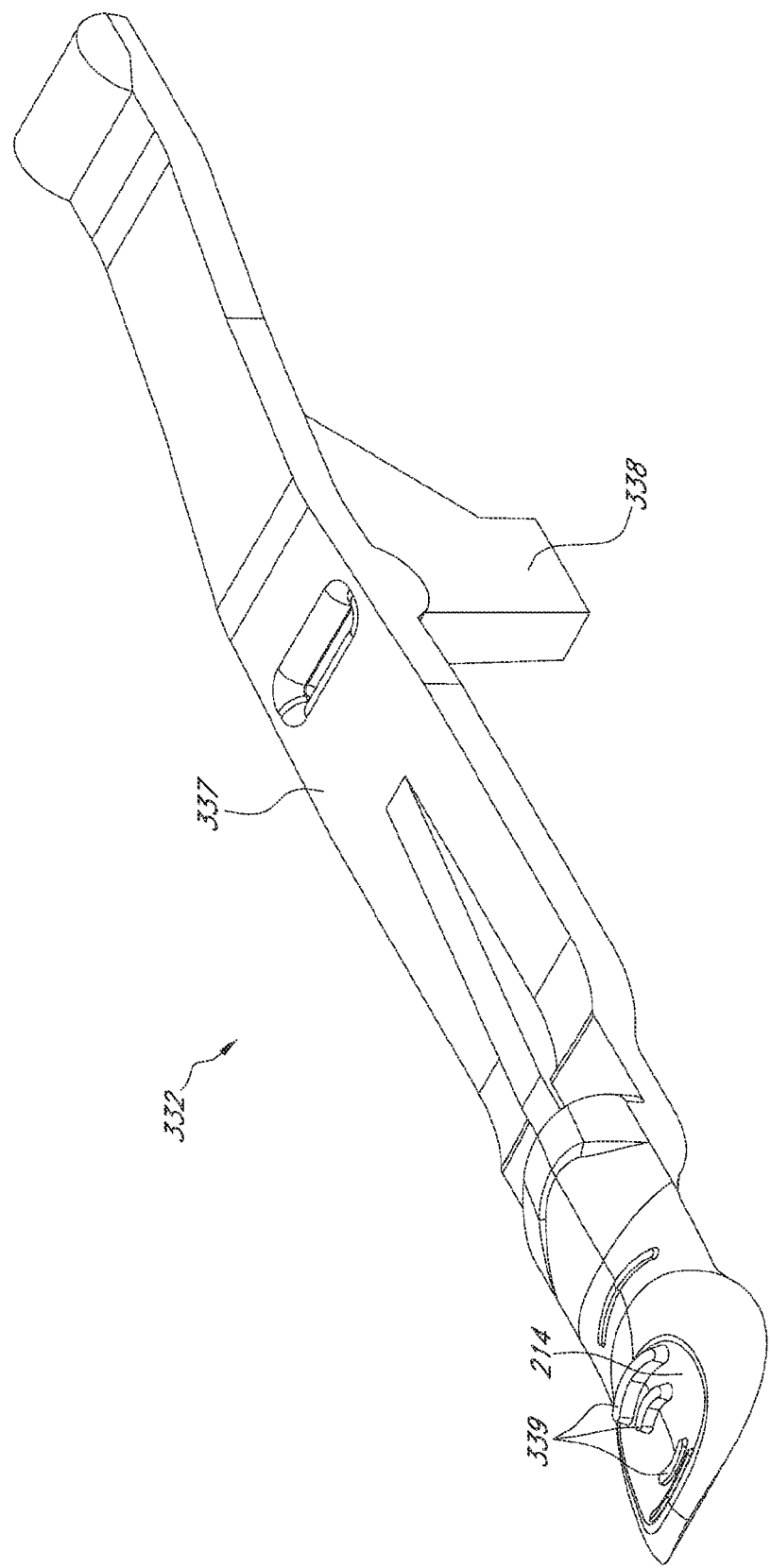
FIG. 10 is a perspective view of the needle retraction button assembly illustrated in FIG. 3.

FIG. 10 is an enlarged perspective view of the needle retraction unit 332 illustrated in FIG. 3. The needle retraction unit 332 includes the needle retraction button 214, a body 337, and an anchor 338. The needle retraction button 214 can advantageously include tactile ridges 339 to increase the friction between the user's finger and the needle retraction button 214 for ease of operation. The anchor 338 extends below the body 337 and is sized and shaped to interface with a corresponding slot of the needle retraction link 335 upon assembly.

FIGS. 11A and 11B illustrate the needle retraction link 335. The needle retraction link 335 is configured to interface with the needle holder 312, the needle retraction unit 332, and the needle retraction spring 334, in order to enable retraction of the needle 208 for delivery of the implants within the eye tissue. The link 335 interfaces with the needle holder 312 via the needle holder coupler 1116. As shown, the needle holder coupler 1116 matches the profile of the needle retraction link slot 316 shown in FIG. 6A. The link 335 interfaces with the anchor 338 of the needle retraction unit 332 via anchor slot 1138, which is sized and shaped to receive the anchor 338. The link 335 also interfaces with the distal end of the needle retraction spring 334 via retraction spring slot 1134. The link 335 can be constructed of any rigid material, such as plastic or polymer. In certain embodiments, the link 335 is molded from Vectra® LCP manufactured by Ticona; however, other polymeric materials can be used as desired (for example, neoprene, nylon, polyvinyl chloride (PVC), polystyrene, polyethylene, polypropylene, polyacrylonitrile, silicone, polyvinyl butyral (PVB), acrylonitrile butadiene styrene (ABS)).

FIGS. 12A-12D illustrate further structural details of the trigger unit 351, which includes the trigger button 216, a trigger spring coupling member 355, a trigger dowel pin slot 356, trigger button extensions 357, and a trigger opening 358. The trigger button 216 is sized and shaped to be pressed by a user's finger. In certain embodiments, the trigger button 216 includes tactile ridges or grooves to provide a more secure grip or feel for the user.

The trigger spring coupling member 355 is sized and shaped to be coupled to the proximal end of the trigger button spring 352. In certain embodiments, the trigger button spring 352 can be a leaf spring constructed of a metal, such as stainless steel. The trigger button spring 352 can provide a bias force that returns the trigger button 216 to its initial non-depressed position after it is released by the user. The trigger button spring 352 can be replaced by any other suitable mechanism for providing a return bias force in other embodiments.

The trigger dowel pin slot 356 is sized and shaped to receive the trigger dowel pin 353 illustrated in FIG. 3. The trigger dowel pin 353 enables attachment of the trigger unit 351 to the external housing 202 and provides a pivot for the trigger unit 351. In one embodiment, the trigger dowel pin 353 is made of stainless steel; however, any rigid material is contemplated (for example, a rigid metal or polymer).

The trigger button extensions 357 are sized and shaped to engage with corresponding engagement members protruding from the left housing 302 and the right housing 304 in order to prevent the trigger button 216 from being pressed too far down within the external housing 202, thereby reducing potential interference with the operation of the internal components of the multiple-implant delivery apparatus 200.

The trigger opening 358 is sized and shaped to receive and interface with the cam 341. The trigger opening 358 includes a cam flat receiving slot 359A, and a trigger stop 359B. The triangular cam flat receiving slot 359A and the trigger stop 359B are sized and shaped to receive and temporarily engage flats disposed on the sides of the cam 341 (illustrated as 347 in FIG. 13A), thereby preventing further rotation of the cam 341 and deployment of more than one implant upon a single press of the trigger button 216. In certain embodiments, the width of the trigger stop 359B is from about 0.025 inches to about 0.25 inches; however, any suitable dimensions for engaging with the cam flats are contemplated. In certain embodiments, the trigger button unit 351 is formed of a contiguous, moldable plastic piece. For example, the trigger button unit 351 can be molded from Vectra® LCP manufactured by Ticona; however, other polymeric materials can be used as desired (for example, neoprene, nylon, polyvinyl chloride (PVC), polystyrene, polyethylene, polypropylene, polyacrylonitrile, silicone, polyvinyl butyral (PVB), acrylonitrile butadiene styrene (ABS)).

Figure 13B:
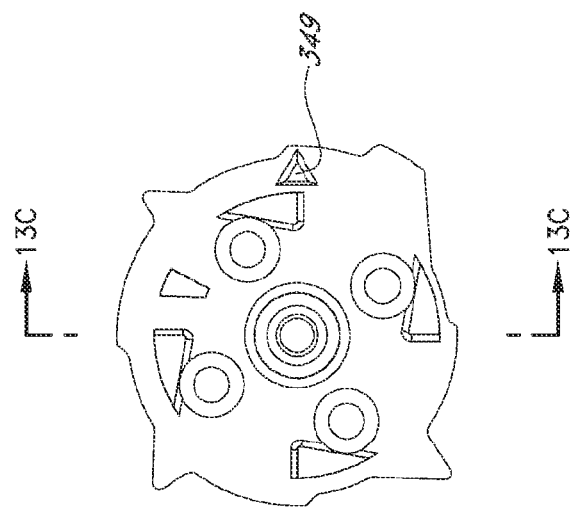
FIG. 13B is a side view of the cam assembly of FIG. 13A.
Figure 13C:
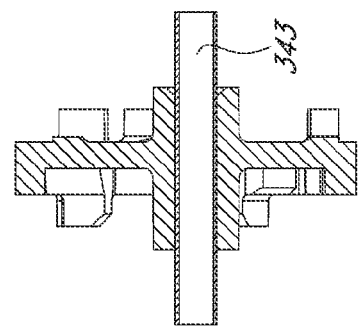
FIG. 13C is a transverse cross-section of the cam assembly of FIG. 13B, in accordance with an embodiment.
Figure 13A:
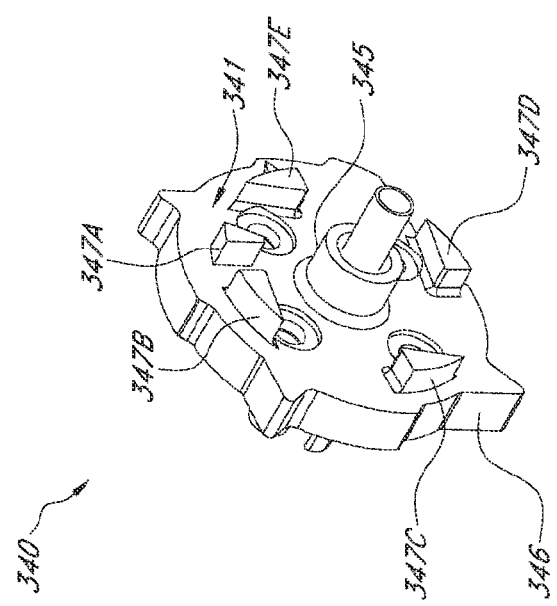
FIG. 13A is a perspective view of the cam assembly of the multiple-implant delivery apparatus of FIG. 2.

FIGS. 13A-13D illustrate a cam assembly 340 in further detail. FIG. 13A is a perspective view of the cam 341 mounted on the cam dowel pin 343. The cam 341 includes a cam hub 345, a contoured cam profile 346, and a plurality of cam flats 347. The cam hub 345 is sized and shaped to receive the cam dowel pin 343, which mounts the cam 341 to the external housing 202 and provides a rotational pivot for rotation of the cam 341. In one embodiment, the cam dowel pin 343 is formed of stainless steel; however, other suitable rigid materials are contemplated. The contoured cam profile 346 controls the lateral movement of the collet 322, which effects delivery of the individual ocular implants 901. The operation of the cam 341, and its effect on the lateral movement of the collet 322, will be discussed later in connection with FIGS. 16A-16E and FIG. 17. In accordance with several embodiments, the implants are configured to be implanted at a substantially the same depth within the eye tissue at a specific distance from the distal end of the multiple-implant delivery apparatus 200, which depth may be controlled by the structural features of the cam 341 described herein or other features or mechanisms.

As shown, the cam 341 can include five cam flats 347. Four of the cam flats 347B-347E can be positioned 90 degrees apart from each other. In operation, these four cam flats can be positioned to stop the rotation of the cam 341 when they abut against the trigger stop 359B, thereby ensuring that only one implant is deployed when the trigger button 216 is pressed. The fifth cam flat 347A can mark the starting point of cam rotation and can assist with the initial alignment of the cam 341 within the cam opening 358 of the trigger button unit 351 upon assembly. Upon assembly, the trigger stop 359B is placed between cam flat 347A and cam flat 347B, thereby ensuring proper initial alignment.

FIG. 13B is a side view of the right side of the cam 341. Alignment mark 349 facilitates the initial alignment of the cam 341 with the cam follower 324 on the collet holder 321 during assembly. FIG. 13C is a transverse cross-section of FIG. 13B. The cam 341 can be constructed of any suitable rigid material (e.g., plastic, polymer, metal, composite). In certain embodiments, the cam 341 is formed of Ultem®, a polyimide thermoplastic resin.

FIG. 13D is an enlarged partial cross-section of the cam assembly 340, showing the cam 341, the cam spring 342, and the cam dowel pin 343. FIG. 13D also illustrates the interaction between the cam follower 324 disposed on the needle holder 321 and the contoured cam profile 346 In certain embodiments, the cam spring 342 is a right hand torsion spring formed of stainless steel. In certain embodiments, the cam spring 342 can be formed of 7.5 coils of wire having a wire diameter of about 0.015 inches and an outer spring diameter of about 0.3 inches. One end of the cam spring 342 can be attached to the cam 341 and the other end can engage with engagement member 345 disposed on the right housing 304 (as shown in FIG. 5A). The cam spring 342 can be wound upon assembly and represents the stored energy that is transferred to the collet 322 to eject the implants 901.

It should be appreciated by one of ordinary skill in the art, based on the disclosure herein, that the cam assembly 340 is one embodiment of a metering device configured to meter a variable amount of stored energy for the delivery of multiple implants at selected locations within eye tissue. The cam assembly 340 can be replaced with other suitable metering devices in other embodiments, such as a solenoid actuator. It should further be appreciated that the collet 322 can be replaced with other suitable driving members in other embodiments, such as a plunger, a stepper motor, or other device that can be mechanically or electrically activated to deliver energy (stored or not stored).

Assembly

FIGS. 14A and 14B illustrate the assembly of the multiple-implant delivery apparatus 200 and show how all the internal components interact with each other upon placement within the right housing 304 during assembly. It should be appreciated that many methods of assembly can be used to assemble the multiple-implant delivery apparatus 200. One embodiment of a method of assembly follows.

First, the sub-components of the various assemblies are assembled. The cam assembly 340 can be assembled by inserting the cam dowel pin 343 into the cam hub 345 and loading the cam spring 342 onto the right side of the cam 341. The trigger button assembly 350 can be assembled by inserting the trigger dowel pin 353 into the trigger dowel pin slot 356 of the trigger button unit 351 and then attaching the trigger spring 352 to the trigger spring coupling member 356 of the trigger button unit 351. The needle assembly 310 can be assembled by attaching (e.g., bonding) the needle 208 to the needle holder 312. The trocar assembly 800 can be assembled by attaching (e.g., welding) the backup tube 816 to the trocar 814. The collet holder assembly 320 can be assembled by attaching (e.g., bonding) the collet 322 to the collet holder 321 and then loading the collet return spring 323 over the collet 322.

After assembling the individual subcomponents, the subcomponents are assembled together and placed within the right housing 304. First, the ocular implants 901 can be loaded onto the trocar assembly 800 and the trocar assembly 800 can be loaded into the collet holder assembly 320. The collet 322 can then be loaded within the insertion tube 903, which in turn can be loaded into the needle assembly 310. The cam assembly 340 can then be placed into the right housing 304 by inserting the right end of the cam dowel pin 343 into the right cam mount 344B. Next, the trigger button assembly 350 can be attached to the right housing 304 by inserting the right end of the trigger dowel pin 353 into the right trigger mount 354A.

After the cam assembly 340 and the trigger button assembly have been placed in the right housing 304, the cam 341 can be wound and the trigger button unit 351 can be set. Then, the collet holder 341, along with the attached needle assembly and trocar assembly, can be placed into the right housing 304 and the cam follower 324 can be aligned with the alignment mark 349 on the cam 341. The collet return spring 323 can be set and the distal end of the collet 322 can be aligned with the distal end of the first of the implants 901 to be delivered. After the collet has been initially positioned, the trocar assembly 800 and the insertion tube 903 can be attached (e.g., bonded) to the right housing 304 using, for example, UV light adhesive bonding methods.

Next, the needle retraction link 335 and the needle retraction button unit 332 can be placed within the right housing 304. The anchor 338 of the needle retraction button unit 332 can be inserted within the anchor slot 1138 of the needle retraction link 335 and the needle holder coupling member 1116 can be inserted within the link slot 316 of the needle holder 312. The needle retraction spring 334 can then be attached to the needle retraction link 335 via the needle retraction spring slot 1134 and to the needle retraction spring mount 336B of the right housing 304.

Finally, the left housing 302 can be snapped onto the right housing 304 via snap-fit members 308 and the left and right fasteners 305 are inserted into their respective fastener slots 366.

Operation of Multiple-Implant Delivery Apparatus

Figure 15:
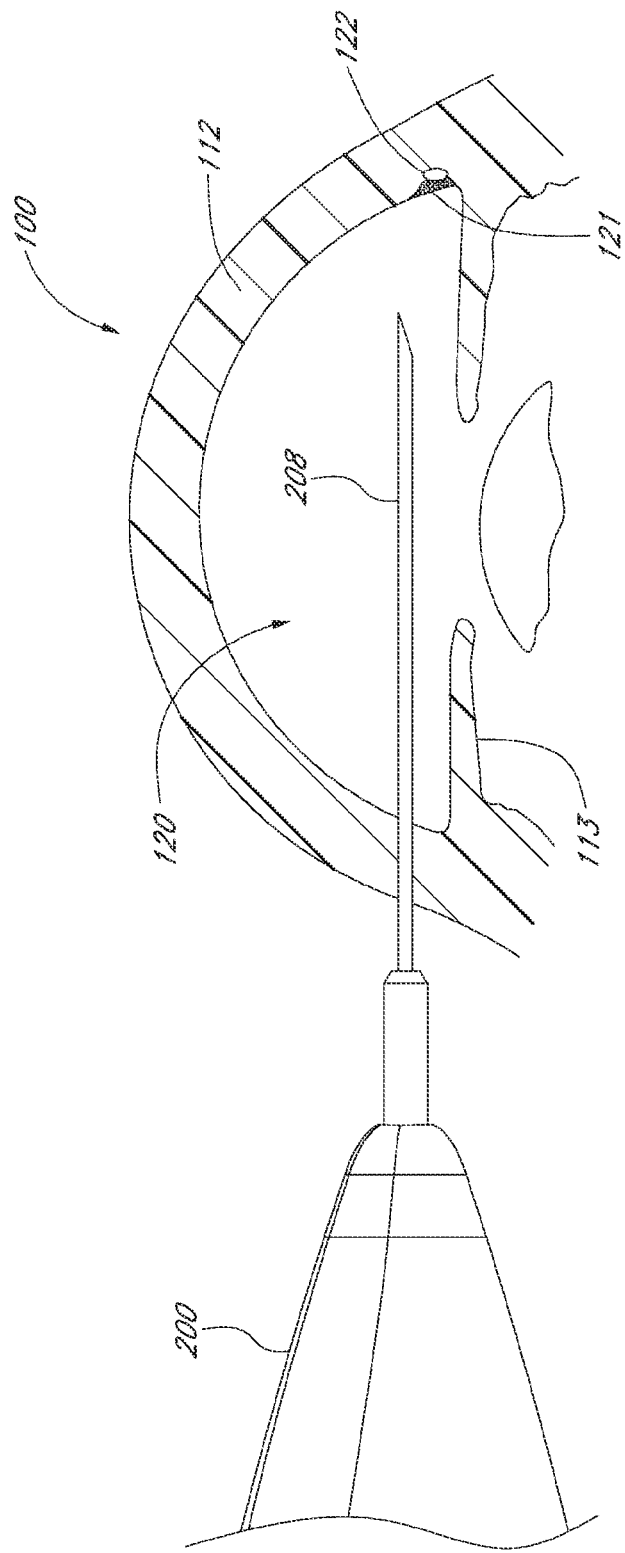
FIG. 15 is a schematic and partial sectional view of a portion of an eye illustrating insertion of the multiple-implant delivery apparatus 200 within the eye 100 using an ab interno procedure, in accordance with an embodiment.

FIG. 15 illustrates the insertion of the multiple-implant delivery apparatus 200 within the eye 100 using an ab interno procedure. In one embodiment of implant delivery, the patient is placed in the supine position, prepped, draped and anesthesia obtained. In one embodiment, a small self-sealing (e.g., less than 1 mm) incision or opening is made in the cornea 112 at or near the limbus or in other external surface area of the eye. In certain embodiments, the needle 208 is inserted from a site transocularly situated from the desired implantation site. The needle 208 is then advanced through the corneal incision across the anterior chamber 120 toward the desired implantation site within the trabecular meshwork 121 under gonioscopic (lens) or endoscopic guidance. Although FIG. 15 illustrates an ab interno method of insertion, it should be appreciated that ab externo methods of insertion are also contemplated.

Upon reaching the vicinity of the desired implantation site adjacent the trabecular meshwork 121, the user presses the needle retraction button 214 and the needle 208 is retracted toward the external housing 202 and away from the implantation site, thereby exposing the trocar 814, the collet 322, and the insertion tube 903 and inhibiting the needle 208 from causing internal damage to the eye 100. Manual depression of the needle retraction button 214 causes the needle retraction spring 334, which is in tension, to compress and cause the needle retraction link 335 to be retracted toward the proximal end of the multiple-implant delivery apparatus 200. The retraction of the needle retraction link 335 results in the retraction of the needle 208, due to the coupling of the needle retraction link 335 with the needle holder 312. The cutting tip 818 of the trocar 814 is then used to create an opening within the trabecular meshwork 121 at the desired implantation site. The cutting tip 818 of the trocar 818 is then advanced until it resides within Schlemm's canal or another physiologic outflow pathway. The advancement position can be determined by visualization (e.g., imaging or fiberoptic) or tactile methods or by depth markings or a depth stop. At this point, the first implant is ready to be delivered to the desired implantation site upon depression of the trigger button 316 by the user.

Figure 16A:
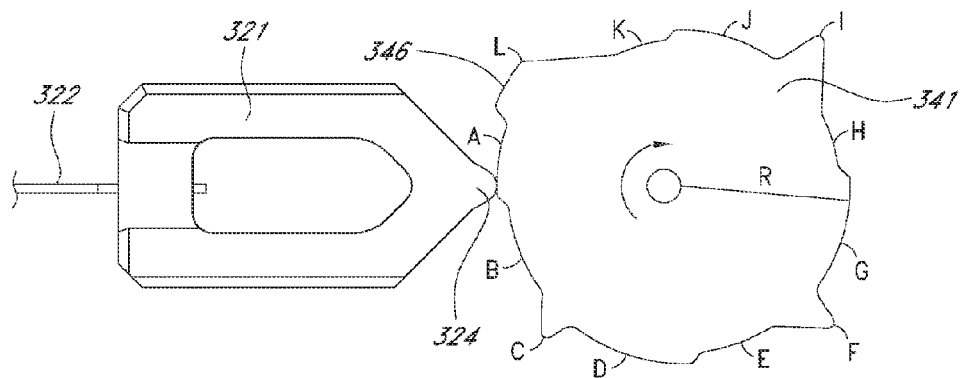
FIGS. 16A-16E illustrate the functional operation of the cam and the collet to effectuate delivery of multiple implants using the multiple-implant delivery apparatus of FIG. 2.

FIGS. 16A-16E illustrate the functional operation between the cam 341 and the collet 322 in effecting delivery of the ocular implants 901. As shown in FIG. 16A, the cam follower 324 abuts against the surface of the contoured profile 346 of the cam 341. As the cam 341 rotates in a clockwise manner, the variations in the contoured cam surface 346 cause the distal end of the collet 322 to move forward and backward along the longitudinal axis of the trocar 814. The change in the radial length R as the cam 341 rotates, due to the variations in the cam contoured surface 346, imparts linear axial motion to the collet 322 corresponding to the change in radial length. When R increases as the cam 341 rotates, the distal end of the collet 322 is driven toward the distal end of the trocar 814. When R decreases as the cam 341 rotates, the distal end of the collet 322 is retracted within the insertion tube 903 and away from distal end of the trocar 814.

FIG. 16A illustrates twelve distinct points along the surface of the contoured profile 346 of the cam 341. Each of the twelve points has an associated radial length that translates into a corresponding lateral position of the distal end of the collet 322. The radial length at firing points C, F, I and L can advantageously be the same to ensure that the distal end of the collet 322 axially translates to the same travel endpoint position during delivery of each successive implant. However, the rising slope of peaks C, F, I and L can advantageously change to ensure that a substantially constant velocity is maintained during delivery of each successive implant. In some embodiments, the substantially constant velocity results in substantially the same implantation depth for each successive implant.

Figure 16B:
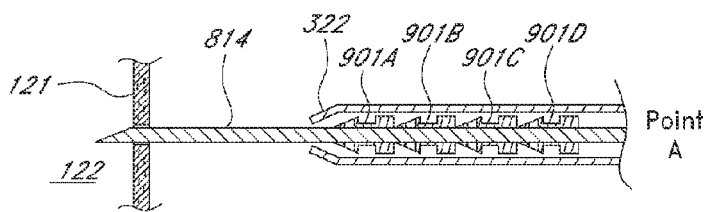
Figure 16C:
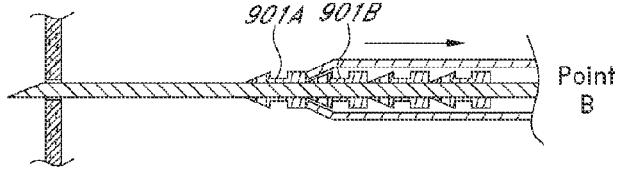
Figure 16D:
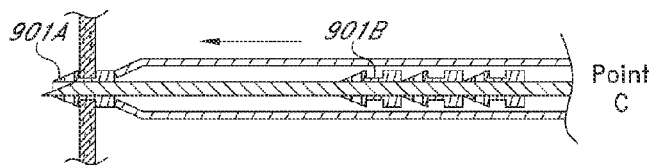

FIGS. 16B-16D illustrate the delivery of a first implant 901A at a first desired implantation site. FIG. 16B illustrates the initial starting position (point A) of the distal end of the collet 322 before the trigger button 216 is pressed for the first time by the user. As shown, the trocar 814 has been advanced through the trabecular meshwork 121 at the desired implantation site. In the illustrated embodiment, the implants 901 are arranged in tandem along the longitudinal axis of the trocar 814. Each of the implants 901 includes an inner lumen through which at least a portion of the trocar 814 extends. The initial starting point of the distal end of the collet 322 corresponds with the front end of the first implant 901A and can be spaced from the distal end of the trocar 814.

Manual depression of the trigger button 216 releases the engagement between the trigger stop 359B and the first cam flat 347B, thereby allowing the cam 341 to freely rotate about the cam dowel pin 343 due to the spring force provided by the wound cam spring 342. As the cam 341 rotates due to the unwinding of the cam spring 342, the cam follower 324 of the collet holder 321 follows the contoured cam surface 346, thereby causing the collet 322 to move laterally as a result of the change in the radius R.

FIG. 16C illustrates the position of the distal end of the collet 322 after the trigger button 216 has been pressed by the user and the cam 341 has rotated to point B. As shown, the distal end of the collet 322 has been retracted (due to the slight decrease in the radial length of the cam 341 between point A and point B and due to the bias force provided by the collet return spring 323) to a position between the proximal end of the first implant 901A and the distal end of a second implant 901B. At point B, the collet 322 engages the proximal end of the first implant 901A, effectively isolating, or "singulating," the first implant 901A for delivery. More specifically, as the collet return spring 323 biases the collet 322 away from the distal end of the trocar 814 due to the rotation of the cam 341 from point A to point B, the slots of the slotted sleeve 328 are caused to open and expand, thereby allowing the collet 322 to move over the first implant 901A.

FIG. 16D illustrates the position of the distal end of the collet 322 when the cam 341 has rotated to point C. The radius at point C is greater than the radius at point B, resulting in the axial translation of the collet 322 to the position depicted in FIG. 16D. As shown, the first implant 901A has been ejected from the trocar 814 due to the driving force of the collet 322 and now sits securely in the desired implantation site spanning the trabecular meshwork 121. The travel distance of the distal end of the collet 322 is determined by the difference in radial length between points B and C and the delivery velocity is determined by the slope between point B and point C. The radial length at point C determines the travel end position of the collet 322 and the slope of the peak rising up to point C determines how fast the distal end of the collet 322 reaches the travel end position.

Figure 16E:
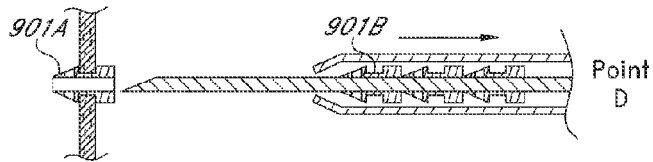

FIG. 16E illustrates the position of the distal end of the collet 322 after the trigger button 216 has been released by the user and returned to its initial non-actuated state, due to the bias force provided by trigger spring 352. At point D, the triangular cam flat receiving slot 359A and the trigger stop 359B have engaged the next cam flat 347C, thereby inhibiting further rotation of the cam 341 until the trigger button 216 is pressed again by the user. As shown, the distal end of the collet 322 has been retracted backward (due to the decrease in radial length from point C to point D and due to the collet return spring 323) to a point corresponding to the distal end of the second implant 901B. It should be appreciated that the distal position of the collet 322 at point D can be identical to the distal position of the collet 322 at point B, by configuring the radius R of the cam 341 to be substantially the same at points B and D.

As further shown in FIG. 16E, the trocar 814 can be removed from the first implantation site in the internal eye tissue. The multiple-implant delivery apparatus 200 can then be moved to a second desired implantation site for delivery of the second implant 901B within the same eye. Thus, the multiple-implant delivery apparatus 200 can advantageously deliver multiple ocular implants at multiple locations within the eye without necessitating removal of the needle 208 or trocar 814 from the eye to reload another implant.

The contoured cam surface 346, in certain embodiments, is advantageously designed to deliver each of the implants 901 at a substantially constant delivery velocity to ensure repeatability and consistency in deployment (e.g., controlled extension distance or implantation depth) of the ocular implants between implantation sites within the same eye and within eyes of different patients. It should be appreciated by one of ordinary skill in the art, upon reading this disclosure, that in order to drive the collet 322 over a longer distance, more stored energy must be transmitted to the collet 322 by the cam spring 342. The amount of energy transmitted is controlled by varying the slope of each of the four firing peaks (C, F, I and L) disposed on the contoured cam surface 346. As best illustrated in FIG. 16A, the length and steepness of the rising slope varies for each of the firing peaks in order to control the amount of energy transmitted by the cam spring 342 to the collet 322. The change in slope also ensures that each successive implant is delivered with a substantially constant delivery velocity. The desired delivery velocity can be calculated to eject the implant at a velocity sufficient to position the implant so that the distal end of the implant resides within Schlemm's canal 122 (but not so far within Schlemm's canal 122 that the distal end of the implant comes in contact with the outer wall of Schlemm's canal 122) and so that the proximal end of the implant remains exposed to the anterior chamber 120 (as shown in FIG. 18). For the embodiments of the multiple-implant delivery apparatus 200 and the implants 901 described herein, the ejection velocity required to obtain a successful implantation is from about 4,000 mm/sec to about 30,000 mm/sec, including about 9,000 mm/sec to about 12,000 mm/sec and about 11,000 mm/sec.

Figure 17:
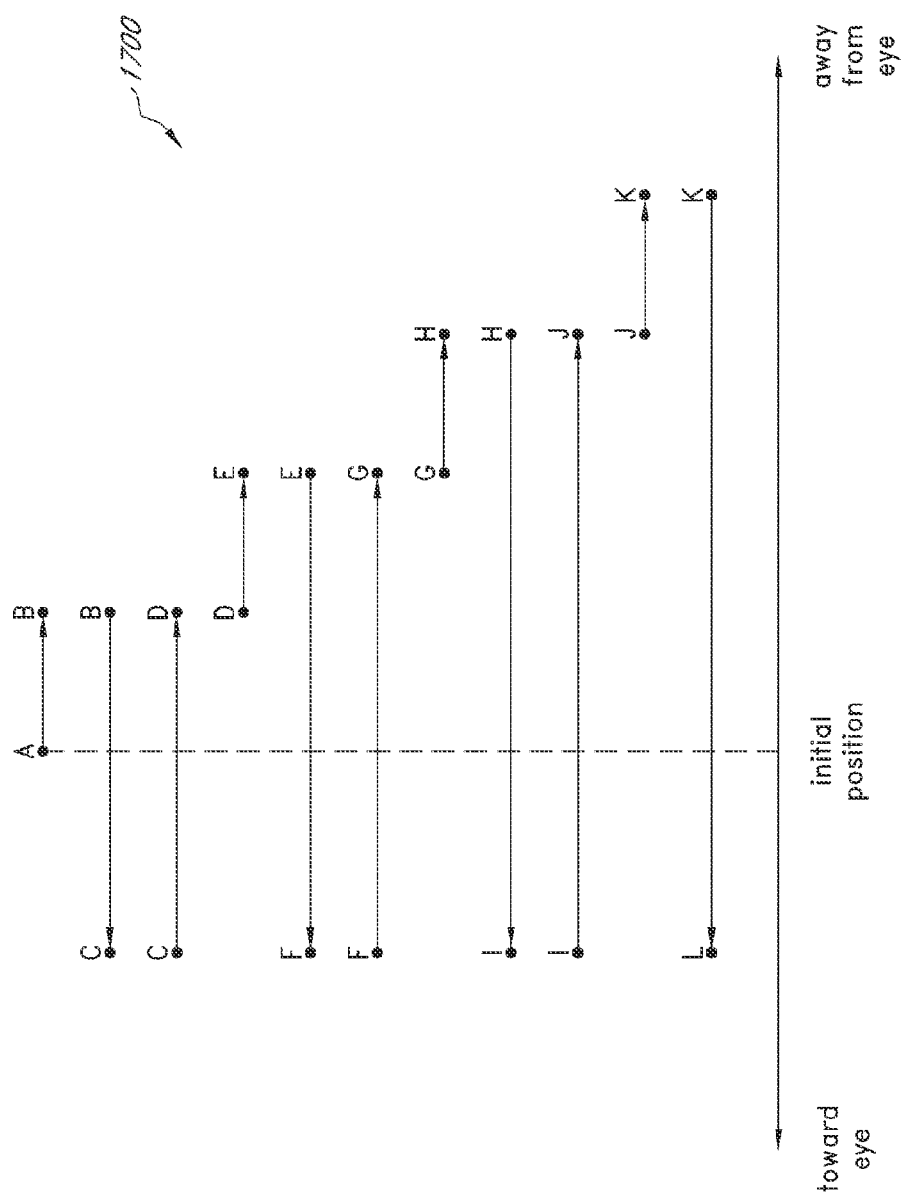
FIG. 17 illustrates how rotational movement of a cam with the contoured surface profile of FIG. 16A translates into lateral motion of a driving member, in accordance with an embodiment.

FIG. 17 illustrates the position of the distal end of the collet 322 at each of the twelve points labeled in FIG. 16A. As shown, because the implants are arranged serially in tandem, the distance required to be travelled by the collet 322 increases for each successive delivery cycle. For example, the distance travelled by the collet 322 as the cam 341 rotates from point E to point F to deliver the second implant 901B is greater than the distance travelled by the collet 322 as the cam 341 rotates from point B to point C to deliver the first implant 901A. As further shown, the travel end position of the distal end of the collet 322 can be the same at each of the four firing points C, F, I, and L by having the radial length of the cam 341 be substantially the same at each of the four firing points. In other embodiments, the radial length at each of the firing points can be different.

With continued reference to FIG. 17, the position of the distal end of the collet 322 is identical at the points on each side of the four firing peaks in order to ensure isolation, or singulation, of the next implant. This can be achieved by configuring the contoured cam surface 346 such that the radial length is substantially the same at the points immediately before and after delivery. For example, as shown, the position of the distal end of the collet 322 is the same at points B and D, E and G, and H and J. In other embodiments, the contoured cam surface 346 can be configured such that the collet 322 does not return to the point before the previous delivery (at the distal end of the next implant), but instead is retracted all the way back to the proximal end of the next implant.

In some embodiments, the multiple-implant delivery apparatus 200 can include a seal to prevent aqueous humor from passing through the multiple-implant delivery apparatus 200 and/or between the members of the multiple-implant delivery apparatus 200 when the instrument is in the eye. The seal can also aid in preventing backflow of aqueous humor through the multiple-implant delivery apparatus 200 and out the eye. Suitable seals for inhibiting leakage include, for example, an o-ring, a coating, a hydrophilic agent, a hydrophobic agent, and combinations thereof. The coating can be, for example, a silicone coat such as MDX™ silicone fluid. In some embodiments, the multiple-implant delivery apparatus 200 is coated with the coating and a hydrophilic or hydrophobic agent. In some embodiments, one region of the apparatus is coated with the coating plus the hydrophilic agent, and another region of the apparatus is coated with the coating plus the hydrophobic agent. The seal can comprise a hydrophobic or hydrophilic coating between slip-fit surfaces of the members of the apparatus. The seal can be disposed proximate of an implant when carried by the multiple-implant delivery apparatus 200 In accordance with several embodiments, the seal is advantageously present on at least a section of each of two devices that are machined to fit closely with one another. In various embodiments, the seal is present on at least an inner surface of the insertion tube 1902, an outer surface of the collet 322, or both.

Although the operation of the multiple-implant delivery apparatus 200 has been described in conjunction with a cam as the metering device and a collet as the driving member, it should be appreciated that other suitable metering devices and driving members can be used to accomplish the delivery of multiple implants at a constant velocity. In addition, although the operation of the multiple-implant delivery apparatus 200 has been described in conjunction with a wound cam torsion spring providing the stored energy that is transmitted to the collet, it should be appreciated that other suitable stored energy sources can be used to transmit energy to a driving member (e.g., relaxation of a non-torsion spring such as a compression spring).

Implants

As used herein, "implants" refers to ocular implants which can be implanted into any number of locations in the eye. In some embodiments, the ocular implants are drainage implants designed to facilitate or provide for the drainage of aqueous humor from the anterior chamber of an eye into a physiologic outflow pathway in order to reduce intraocular pressure. In some embodiments, the implant can be sized and shaped to provide a fluid flow path for draining aqueous humor from the anterior chamber through the trabecular meshwork and into Schlemm's canal. In other embodiments, the implant can be configured to provide a fluid flow path for draining aqueous humor from the anterior chamber to a uveoscleral outflow pathway. In some embodiments, the aqueous humor is diverted to the supraciliary space or the suprachoroidal space of the uveoscleral outflow pathway.

The term "implant" as used herein is a broad term, and is to be given its ordinary and customary meaning to a person of ordinary skill in the art (and it is not to be limited to a special or customized meaning), and refers without limitation to drainage shunts, stents, sensors, drug delivery implants, drugs, therapeutic agents, fluids, or any other device or substance capable of being inserted within an eye.

In certain embodiments, one or more of the implants are ocular implants for purposes other than drainage (for example, a drug delivery device or an ocular sensor for measuring intraocular pressure or components of ocular fluid, such as glucose). In some embodiments, an implant comprises two sections or portions tethered together, such as a sensor tethered to a drainage implant, a sensor tethered to an anchor.

In some embodiments, drainage implants define one or more fluid passages. The fluid passage(s) in some embodiments remains patent and, in other embodiments, the passage(s) is fully or partially occluded under at least some circumstances (e.g., at lower intraocular pressure levels). The implants may feature a variety of characteristics, described in more detail below, which facilitate the regulation of intraocular pressure. The mechanical aspects and material composition of the implant can be important for controlling the amount and direction of fluid flow. Therefore, various examples of implant dimensions, features, tip configurations, material flexibility, coatings, and valve design, in accordance with some embodiments of the present disclosure, are discussed in detail below. While ocular implants will be described herein, it should be appreciated that other types of implants can be used by embodiments of the systems and methods described herein for implantation into other body tissue or body cavities. The term "implant" can be interchanged with the words "stent" or "shunt" in various embodiments.

FIG. 18 is an enlarged schematic and partial sectional view of Schlemm's canal 122 and the trabecular meshwork 121 of the eye 100 illustrating the implantation position and the operation of one type of implant 901 that may be delivered by the multiple-implant delivery apparatus 200. As shown, the implant 901 is delivered such that the proximal end 902A is positioned within the anterior chamber 120 and the distal end 902B of the implant is positioned within Schlemm's canal 122. Accordingly, the multiple-implant delivery apparatus 200 can be configured to deliver the implant 901 so that the distal end 902B penetrates through the trabecular meshwork and the inner wall 912 of Schlemm's canal 122 without penetrating through the outer wall 914 of Schlemm's canal 122.

The implant 901 is a substantially axisymmetric implant. The implant 901 can be divided for description purposes into a proximal portion 904, an intermediate portion 905, and a distal portion 907. The lumen 908 can extend from a proximal end 902A through each of the portions to a distal end 902B of the implant 901 and is configured to provide fluid communication between the proximal and distal ends. The lumen 908 defines an axis upon which the three portions of the implant 901 are serially aligned.

The proximal portion 904 is generally cylindrical with the lumen extending therethrough. The proximal end 902A of the implant 901 can comprise a generally flat surface that defines an opening in the middle thereof to provide fluid communication between the exterior of the proximal portion 904 and the lumen 908. The exterior surfaces of the proximal portion 904 can be generally smooth, and the edge between the proximal end 902A and the sides of the proximal portion 904 can be generally rounded, beveled or sharpened. In embodiments where the edge between the proximal end 902A and the sides of the proximal portion 904 is sharpened, the sharpened edge may prevent or reduce the likelihood of fibrosis from growing up and over the edge and into the inlet, thereby clogging flow. The proximal portion 904 can have a cross-sectional measurement (e.g., a diameter) of between about 0.01 mm and about 0.5 mm (0.2 mm, for example), and the opening can have a cross-sectional measurement of about 0.001 mm to about 0.4 mm (0.08 mm, for example). The implant 901 can be between about 0.01 and 1 mm long (0.3 mm, for example) from the proximal end 902A to its distal end 902B.

The intermediate portion 905 can also be generally cylindrical, aligned along the same axis as the proximal portion 904, and can have a reduced cross-sectional measurement relative to the proximal portion 904. Accordingly, the intermediate portion 905 can have a cross-sectional measurement ranging between about 0.001 mm to about 0.4 mm (0.1 to 0.18 mm, for example). The lumen 908 extends through the intermediate portion 905 along the same axis as through the proximal portion 904 and has a cross-sectional measurement of between about 0.001 mm to about 0.4 mm (0.08 mm, for example). The exterior surfaces of the intermediate portion 905 can be generally smooth, and the portion's junctions with the proximal portion 904 and the distal portion 907 can be generally rounded, chamfered, beveled sharpened, or have a substantially defined edge. In other embodiments, the intermediate portion 905 and the proximal portion 904 can have the same cross-sectional dimension such that the two portions essentially form a single portion.

The distal portion 907 of the implant 901 can also be generally aligned along the same axis as the proximal portion 904 and the intermediate portion 905 and can have a generally frustoconical exterior configuration. The proximal end of the distal portion 907 can comprise a flat, annular surface that extends from the junction of the intermediate portion 905 at about ninety degrees and extends to the edges of the proximal end. The cross-sectional measurement at the proximal end of the distal portion 907 can be about 0.05 to about 0.5 mm (about 0.2 mm, for example). The sides of the distal portion 907 extend distal of its proximal end in a tapered configuration, similar to that of a cone. The sides of the distal portion 907 are tapered until the sides terminate at the distal end upon meeting the lumen that extends through the implant 901, thus forming a frustoconical shape having a flat distal end. The sides of the distal portion 907 can include openings or apertures (e.g., outlet ports 906) positioned circumferentially along the frustoconical distal portion 907 that provide fluid communication between the exterior of the distal portion 907 and the lumen 908 extending through the implant 901. The surface of the distal end of the distal portion 907 can include an outlet or aperture that is axially aligned with the lumen of the distal portion 907 (not shown). The lumen that extends through the distal portion 907 of the implant 901 is preferably axially aligned with the lumen extending through both the proximal and intermediate portions.

Referring to FIG. 18, the aqueous humor flows from the anterior chamber 120, through the inlet lumen 908, and then out through one, two or more of four side outlet ports (906A. 906B, 906C and a fourth outlet port opposite outlet port 906C) to be directed in both directions along Schlemm's canal 122. In some embodiments, the implant 901 includes an axial outlet port in communication with the inlet lumen 908 that is located along a distal end 902B to potentially direct flow in an axial direction if the distal end 902B is not obstructed. Alternatively, flow could be directed in only one direction through a single outlet port 906A or flow could be directed in two directions through two outlet ports 906A and 906B, depending on a rotational position of the implant 901 within Schlemm's canal or other physiologic outflow pathway upon implantation. In other embodiments, more than two outlet ports 906 can be efficaciously used, as needed or desired to increase outflow or reduce the potential for obstruction of the outlet ports to flow within Schlemm's canal 122. For example, in some embodiments, four outlet ports 906A, 906B, 906C and a fourth outlet port opposite outlet port 906C can be oriented at 90 degrees with respect to the inlet lumen 908 and with respect to adjacent outlet ports such that an outlet port is positioned at every 90 degree rotation of the implant 901. The use of four or more outlet ports may increase the likelihood that at least two outlet ports are oriented to facilitate flow within Schlemm's canal 122 without rotational adjustment or orientation after delivery or implantation. The proximal end of the distal portion 907 can abut the inner wall 912 of Schlemm's canal 122, and the distal end of the proximal portion 904 can abut the trabecular meshwork 121 upon delivery. Accordingly, the implant 901 can be secured in place by the proximal and distal portions of the implant 901 abutting opposite sides of the trabecular meshwork 121. In some embodiments, the distal end 902B is in contact with the outer wall 914 of Schlemm's canal 122. In some embodiments, an additional axial outlet is located at the distal end 902B. In such embodiments, the main lumen 908 may also be in fluid communication with this additional axial outlet. In some instances, the axial outlet is non-functional because it is in contact with a wall of Schlemm's canal when implanted, and therefore outflow through the axial outlet is blocked. In alternative embodiments, the implant 901 can be implanted such that an outlet of the implant 901 is positioned in a physiologic outflow pathway other than Schlemm's canal 122.

At least some of the disclosed embodiments include implants that provide a fluid flow path for conducting aqueous humor from the anterior chamber of an eye to a physiologic outflow pathway to reduce intraocular pressure, preferably below episcleral venous pressure without hypotony. The implants can have an inflow portion and an outflow portion. The outflow portion of the implant preferably is disposed at or near a distal end of the implant. When the implant is implanted, the inflow portion may be sized and configured to reside in the anterior chamber of the eye and the outflow portion may be sized and configured to reside in a physiologic outflow pathway. In some embodiments, the outflow portion may be sized and configured to reside in Schlemm's canal. In other embodiments, the outflow portion may be sized and configured to reside at least partially in the supraciliary region of the uveoscleral outflow pathway or the suprachoroidal space.

One or more lumens can extend through the implant to form at least a portion of the flow path. In some embodiments, there is at least one lumen that operates to conduct the fluid through the implant. Each lumen preferably extends from an inflow end to an outflow end along a lumen axis. In some embodiments the lumen extends substantially through the longitudinal center of the implant. In other embodiments, the lumen can be offset from the longitudinal center of the implant. In still other embodiments, the flow path can be defined by grooves, channel or reliefs formed on an outer surface of the implant body.

One or more openings can extend through the wall of the implant. In some embodiments, the openings can extend through a middle portion of the implant. In other embodiments the openings can extend through other portions of the implant. The openings can be one or more of a variety of functions. One such function is that when the implant is inserted into the physiologic outflow pathway, the openings provide a plurality of routes through which the aqueous humor can drain. For example, once the implant is inserted into the eye, if the implant only has one outflow channel (e.g., one end of a lumen), that outflow channel can be plugged, for example, by the implant's abutment against the outer wall of Schlemm's canal or against the interior surface of the sclera or the outer surface of the choroid. Additionally, the outflow channel can be clogged with tissue that is accumulated or cored during the advancement of the implant through the fibrous or porous tissue. A plurality of openings can provide a plurality of routes through which the fluid may flow to maintain patency and operability of the drainage implant. In embodiments where the implant has a porous body, the openings can define surface discontinuities to assist in anchoring the implant once implanted.

The implant in some embodiments can include a distal portion that is sufficiently sharp to pierce eye tissue, including eye tissue in the trabecular meshwork or eye tissue near the scleral spur of the eye, and that is disposed closer to the outlet portion than to the inlet portion. In some embodiments, the distal portion is located at the distal end of the implant. In another embodiment, the distal portion can be sufficiently blunt so as not to substantially penetrate eye tissue. In some embodiments, the implants have a generally sharpened forward end and are self-trephinating, i.e., self-penetrating, so as to pass through tissue without pre-forming an incision, hole or aperture. The sharpened forward end can be, for example, conical or tapered. The tip can be sufficiently sharp to pierce eye tissue. The tip also can be sufficiently blunt so as not to substantially penetrate eye tissue. The taper angle of the sharpened end can be, for example, about 30°±15° in some embodiments. The radius of the tip can be about 70 to about 200 microns. In other embodiments, where an outlet opening is formed at the distal end of the implant, the distal portion can gradually increase in cross-sectional size in the proximal direction, preferably at a generally constant taper or radius or in a parabolic manner. In some embodiments including an outlet opening at the distal end, the diameter of the axial outlet opening formed at the distal end may be between 40 and 200 microns (e.g., 40 microns, 60 microns, 80 microns, 100 microns, 120 microns, 120 microns, 140 microns, 160 microns, 180 microns). Additionally, in such embodiments, an annulus may be formed between an edge defined by the outer circumference of the axial outlet opening and an edge defined by the intersection of the distal tip surface and the conical or tapered section of the distal portion. The width of this annulus may advantageously be sufficiently small such that, after the trocar has created a pilot hole in eye tissue (e.g., trabecular meshwork), the distal portion can expand eye tissue surrounding the pilot hole as the implant is advanced into the eye tissue. The eye tissue can then retract around an intermediate portion of the eye implant. If the annulus width is not sufficiently small, the distal portion may potentially push, rather than expand, the eye tissue.

In some embodiments, the body of the implant can include at least one surface irregularity. The surface irregularity can include, for example, a ridge, groove, relief, hole, or annular groove. The surface discontinuities or irregularities can also be formed by barbs or other projections, which extend from the outer surface of the implant, to inhibit migration of the implant from its implanted position. In some embodiments, the projections can include external ribbing to resist displacement of the implant. The surface irregularity in some embodiments can interact with the tissue of the trabecular meshwork or with the interior wall of the sclera and/or with the tissue of the ciliary attachment tissue in order to provide an anchoring function. In some embodiments, the implants are anchored by mechanical interlock between tissue and an irregular surface and/or by friction fit. In other embodiments, the implant includes cylindrical recessed portions (e.g., annular groves) along an elongate body to provide enhanced gripping features during implantation and anchoring following implantation within the eye tissue.

The implant can also incorporate fixation features, such as flexible radial (i.e., outwardly extending) extensions. The extensions may be separate pieces attached to the implant, or may be formed by any suitable method, including slitting the implant wall, and thermally forming or mechanically deforming the extensions radially outward. If the extensions are separate pieces, they can be composed of flexible material such as nitinol or polyimide. The extensions may be located at the proximal or distal ends of the implant, or both, to prevent or resist extrusion of the implant from its intended location. The flexibility of the fixation features will facilitate entry through the corneal incision, and also through the eye tissue.

The implant can also comprise a body structure having one or more surfaces having a plurality of nanostructured components associated therewith. The plurality of nanostructured components can include, for example, carbon nanotubes, nanofibers, nanowires, or nanofibrous mesh. The plurality of nanostructured components enhance one or more of adhesion, non-adhesion, friction, patency or biointegration of the implant with one or more tissue surfaces of a body of a patient. In certain embodiments, the nanostructured components on the surfaces of the implant can be embedded in a biocompatible matrix to hold the nanostructured components together.

In some embodiments, the body of the implant has an outlet opening on a side surface to allow fluid flow. In some embodiments, the body of the implant has a plurality of outlet openings on a side surface to allow fluid flow. In other embodiments, there is a plurality of outlet openings at one end of the implant, such as the distal end. The openings can facilitate fluid flow through the implant.

The implant can in some embodiments have a cap, or tip, at one end. The cap can include a tissue-piercing end and one or more outlet openings. Each of the one or more outlet openings can communicate with at least one of the one or more lumens. In some embodiments, the cap can have a conically shaped tip with a plurality of outlet openings disposed proximal of the tip's distal end. In other embodiments, the cap can have a tapered angle tip. The tip can be sufficiently sharp to pierce eye tissue. The tip also can be sufficiently blunt so as not to substantially penetrate eye tissue in the absence of sufficient force. In some embodiments, the conically shaped tip facilitates delivery of the implant to the desired location. In some embodiments, the cap has an outlet opening on a side surface to allow fluid flow. In some embodiments, the cap has a plurality of outlet openings on a side surface to allow fluid flow. In other embodiments, there is a plurality of outlet openings on the conical surface of the cap. The openings on the cap can facilitate fluid flow through the implant. The opening may provide an alternate route for fluid flow which is beneficial in case the primary outflow portion of the implant becomes blocked.

In some embodiments, multiple implants are configured to be delivered during a single procedure. In some embodiments when multiple implants are delivered, the implants can be arranged in tandem. In one embodiment, the implant can include a tip protector at one end. The tip protector can include a recess shaped to receive and protect, for example, the tip of an adjacent implant. In some embodiments, the tip of the adjacent implant has a conical shape. The recess may be shaped to contact the sides of the conical tip while protecting the more tapered tip, or end, from impact. The tip protector is particularly useful for delivery of multiple implants.

The implants may be of varied lengths and sizes to optimize flows. In some embodiments, the implant has sufficient length such that the outflow portion resides in a physiologic outflow pathway and the inflow portion is exposed to the anterior chamber. In some embodiments, the length of the implant from the portion residing in the anterior chamber to the portion residing in the physiologic outflow pathway may be about 0.001 mm to about 5 mm, about 0.01 mm to about 1 mm, about 0.1 mm to about 0.5 mm, or overlapping ranges thereof. In some embodiments, the length of the implant is about 0.05, 0.10, 0.15, 0.20, 0.25, 0.30, 0.35, 0.40, 0.45, or 0.50 mm.

In some embodiments, the implant can have an outer diameter that will permit the implant to fit within a 23-gauge needle during implantation. The implant can also have a diameter that is designed to be inserted with larger needles. For example, the implant can also be delivered with 18-, 19- or 20-gauge needles. In other embodiments, smaller gauge applicators, such as a 25-gauge (or smaller) applicator, may be used. The implant can have a substantially constant cross-sectional shape through most of the length of the implant, or the implant can have portions of reduced or enlarged cross-sectional size (e.g., diameter), or cylindrical channels, e.g., annular grooves, disposed on the outer surface between the proximal end and the distal end. The distal end of the implant can have a tapered portion, or a portion having a continually decreasing radial dimension with respect to the lumen axis along the length of the axis. The tapered portion preferably in some embodiments terminates with a smaller radial dimension at the outflow end. During implantation, the tapered portion can operate to form, dilate, and/or increase the size of, an incision or puncture created in the tissue. The tapered portion may have a diameter of about 23 gauge to about 30 gauge, and preferably about 25 gauge. However, other dimensions are possible.

The diameter of one or more drainage lumens within the implant may be varied to alter flow characteristics. The cross-sectional size of an implant may be, for example, from about 0.1 mm to about 1.0 mm (for example, from about 0.3 mm to about 0.4 mm). A small cross-sectional size can be used to restrict flow. The cross-sectional shape of the implant or an implant may be any of a variety of cross-sectional shapes suitable for allowing fluid flow. For example, the cross-sectional shape of the implant or implant may be circular, oval, square, trapezoidal, rectangular, or any combination thereof.

In some embodiments, the implant is configured to expand, either radially or axially, or both radially and axially. In some embodiments, the implant may be self-expanding. In other embodiments, the implant may be expanded by, for example, using a balloon device.

In some embodiments, the structure of the implant may be flexible. At least a portion of the structure of the implant may be flexible, or the whole structure may be flexible. In some embodiments, the structure of the implant is accordion- or balloon-like. This pleated like structure provides flexibility. In other embodiments, at least a portion of the implant is curved. In some embodiments, at least a portion of the implant is straight. In some embodiments, the implant has both curved and straight portions, and in some embodiments, the implant is generally rigid (i.e., maintains its preformed shape when implanted).

The implant is preferably made of one or more biocompatible materials. Suitable biocompatible materials include, for example, polypropylene, polyimide, glass, nitinol, polyvinyl alcohol, polyvinyl pyrolidone, collagen, chemically-treated collagen, polyethersulfone (PES), poly(styrene-isobutyl-styrene), Pebax, acrylic, polyolefin, polysilicon, polypropylene, hydroxyapetite, titanium, gold, silver, platinum, other metals, ceramics, plastics and a mixture thereof. The implants can be manufactured by sintering, micro machining, laser machining, and/or electrical discharge machining. However, other suitable manufacturing methods can be used.

In some embodiments, the implant is made of a flexible material. In other embodiments, the implant is made of a rigid material. In some embodiments, a portion of the implant is made from flexible material while another portion of the implant is made from rigid material. The body can have an outer surface of which at least a portion is porous. Some embodiments include porosity that can be varied by masking a portion of the exterior with a band. Where the implants include a porous body, the cross-section and porosity can be calibrated (down to 0.5 micrometers) to control the flow rates of aqueous humor through the implant.

In some embodiments, at least a portion of the implant (e.g., an internal spine or an anchor) is made of a material capable of shape memory. A material capable of shape memory may be compressed and, upon release, may expand axially or radially, or both axially and radially, to assume a particular shape. In some embodiments, at least a portion of the implant has a preformed shape. In other embodiments, at least a portion of the implant is made of a superelastic material. In some embodiments, at least a portion of the implant is made up of Nitinol. In other embodiments, at least a portion of the implant is made of a deformable material.

In some embodiments, the body of the implant can be formed of material that includes a therapeutic agent, and/or can house, anchor, or support a therapeutic agent, or can include a coating. The coating can include a therapeutic agent. The coatings can be, for example, a drug eluting coating, an antithrombogenic coating, and a lubricious coating. The therapeutic agent can be selected from the group consisting of: heparin, TGF-beta, an anti-glaucoma or intraocular pressure-lowering drug, anti-inflammatory agents, antibiotics, pharmaceutical agents, biological agents including hormones, enzyme or antibody-related components, oligonucleotides, DNA/RNA vectors and live cells configured to produce one or more biological components, an anti-proliferative agent, and a vasodilator. Materials that may be used for a drug-eluting coating include parylene C, poly(butyl methacrylate), poly(methyl methacrylate), polyethylene-co-vinyl acetate, and other materials.

In some embodiments, the implant can further include a biodegradable material in or on the implant. The biodegradable material can be selected from the group consisting of poly(lactic acid), polyethylene-vinyl acetate, poly(lactic-co-glycolic acid), poly(D,L-lactide), poly(D,L-lactide-co-trimethylene carbonate), collagen, heparinized collagen, poly(caprolactone), poly(glycolic acid), and a copolymer. All or a portion of the implant may be coated with a therapeutic agent, e.g. with heparin, preferably in the flow path, to reduce blood thrombosis or tissue restenosis.

The flow path through the implant can be configured to be regulated to a flow rate that will reduce the likelihood of hypotony in the eye. In some embodiments, the intraocular pressure is maintained at about 8 mm Hg. In other embodiments, the intraocular pressure is maintained at pressures less than about 8 mmHg, for example the intraocular pressure may be maintained between about 6 mm Hg and about 8 mm Hg. In other embodiments, the intraocular pressure is maintained at pressures greater than about 8 mm Hg. For example, the pressures may be maintained between about 8 mmHg and about 18 mm Hg, and more preferably between 8 mm Hg and 16 mm Hg, and most preferably not greater than 12 mm Hg. In some embodiments, the flow rate can be limited to about 2.5 μL/min or less. In some embodiments the flow rate can be limited to between about 1.9 μL/min and about 3.1 μL/min.

For example, the Hagen-Poiseuille equation suggests that a 4 mm long stent at a flow rate of 2.5 μL/min should have an inner diameter of 52 microns to create a pressure gradient of 5 mm Hg above the pressure in the suprachoroidal space.

The implant may or may not include a mechanism for regulating fluid flow through the implant. Mechanisms for regulating fluid flow can include flow restrictors, pressure regulators, or both. Alternatively, in some embodiments the implant has neither a flow restrictor nor a pressure regulator. Regulating flow of aqueous humor can include varying between at least first and second operational states in which aqueous humor flow is more restricted in a first state and less restricted in a second state. Increasing the restriction to flow when changing from the second state to the first state can involve moving a valve toward a valve seat in a direction generally parallel or generally normal to a line connecting the proximal and distal ends of the implant.

As noted above, the outflow portion of the implant, in some embodiments is sized and configured to reside in the Schlemm's canal. In such embodiments, there is a lesser need for a mechanism for regulating fluid flow through the implant. The mechanism for flow restriction may be, for example, a valve, a long lumen length, small lumen cross section, or any combination thereof. In some embodiments, the flow of fluid is restricted by the size of a lumen within the implant, which produces a capillary effect that limits the fluid flow for given pressures. The capillary effect of the lumen allows the implant to restrict flow and provides a valveless regulation of fluid flow.

In one embodiment, the flow path length may be increased without increasing the overall length of the implant by creating a lumen with a spiral flow path. A lumen within the implant is configured to accommodate placement therein of a spiral flow channel core that is configured to provide flow restriction. In effect, the spiral flow channel provides an extended path for the flow of fluid between the inlet(s) and outlet(s) of the implant that is greater than a straight lumen extending between the ends of the implant. The extended path provides a greater potential resistance of fluid flow through the implant without increasing the length of the implant. The core could have a single spiral flow channel, or a plurality of spiral flow channels for providing a plurality of flow paths through which fluid may flow through the implant. For example, the core can have two or more spiral flow channels, which can intersect.

In some embodiments, the mechanism for flow regulation can include a pressure regulating valve. In one embodiment, the valve can open when fluid pressure within the anterior chamber exceeds a predetermined level (e.g., a preset pressure). Intraocular pressure may be used to apply a force to move a valve surface within the implant in a direction transverse to a longitudinal axis of the implant such that aqueous humor flows from the anterior chamber to an outflow pathway at intraocular pressures greater than a threshold pressure.

In some embodiments, the implant may have any number of valves to restrict flow and/or regulate pressure. The valve can be located between the anterior chamber and one or more effluent openings such that movement of the valve regulates flow from the anterior chamber to the one or more effluent openings. A variety of valves are useful with the implant for restricting flow. In some embodiments, the valve is a unidirectional valve and/or is a pressure relief valve. The pressure relief valve can include a ball, a ball seat and a biasing member urging the ball towards the ball seat. In some embodiments, the valve is a reed-type valve. In a reed valve, for example, one end of the valve may be fixed to a portion of the implant. The body of the reed valve can be deflected in order to allow flow through the valve. Pressure from fluid in the anterior chamber can deflect the body of the reed valve, thereby causing the valve to open.

In some embodiments, the implant can include a pressure regulation valve having a deflectable plate or diaphragm with a surface area exposed to fluid within the anterior chamber, the surface area being substantially greater than the total cross-sectional flow area of the one or more influent openings of the implant. Such a valve can be disposed between an anterior chamber of the implant and the one or more effluent openings such that movement of the deflectable plate regulates flow from the anterior chamber to the one or more effluent openings. The plate can extend in a direction generally parallel to the inlet flow path and to the outlet flow path.

When the intraocular pressure exceeds a predetermined pressure, the check pressure relief valve can open and permit fluid to flow between the anterior chamber and the physiologic outflow pathway. When the intraocular pressure decreases to a second, lower pressure, the valve can close to limit or inhibit fluid from flowing to the physiologic outflow pathway. In one embodiment, the valve can remain closed until the intraocular pressure again reaches the predetermined pressure, at which time the valve can reopen to permit or enhance drainage of fluid to the physiologic outflow pathway. Accordingly, the implant can provide drainage of the anterior chamber through the implant based on the intraocular pressure levels and reduce the likelihood for over-draining the anterior chamber and causing hypotony.

In some embodiments, the implant can provide for delivery of a therapeutic agent or drug. The therapeutic agent can be, for example, an intraocular pressure-lowering drug. In some embodiments, the therapeutic agent or drug is introduced concurrently with the delivery of the shunt to the eye. The therapeutic agent or drug can be part of the implant itself. For example, the therapeutic agent or drug can be embedded in the material of the shunt, or coat at least a portion of the implant. The therapeutic agent or drug may be present on various portions of the implant. For example, the therapeutic agent or drug may be present on the distal end of the implant, or the proximal end of the implant. The implant can include combination of therapeutic agents or drugs. The different therapeutic agents or drugs can be separated or combined. One kind of therapeutic agent or drug can be present at the proximal end of the implant, and a different kind of therapeutic agent or drug can be present at the distal end of the implant.

For example, an anti-proliferative agent may be present at the distal end of the implant to prevent growth, and a growth-promoting agent may be applied to the proximal end of the implant to promote growth.

In some embodiments, the implant includes a chamber or reservoir at least partially filled with a solid or liquid drug or therapeutic agent that can be eluted over time. The drug or therapeutic agent can be located within a lumen of the implant. The release of the drug or therapeutic agent can be controlled by a membrane (which can be porous or non-porous).

Examples of drugs may include various anti-secretory agents; antimitotics and other anti-proliferative agents, including among others, anti-angiogenesis agents such as angiostatin, anecortave acetate, thrombospondin, VEGF receptor tyrosine kinase inhibitors and anti-vascular endothelial growth factor (anti-VEGF) drugs such as ranibizumab (LUCENTIS®) and bevacizumab (AVASTIN®), pegaptanib (MACUGEN®), sunitinib and sorafenib and any of a variety of known small-molecule and transcription inhibitors having anti-angiogenesis effect (additional non-limiting examples of such anti-VEGF compounds are described in Appendix A, which is attached herewith and made a part of this application); classes of known ophthalmic drugs, including: glaucoma agents, such as adrenergic antagonists, including for example, beta-blocker agents such as atenolol, propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluorometholone, loteprednol, medrysone, fluocinolone acetonide, triamcinolone acetonide, triamcinolone, beclomethasone, budesonide, flunisolide, fluticasone, hydrocortisone, hydrocortisone acetate, loteprednol, rimexolone and non-steroidal anti-inflammatory agents including, for example, diclofenac, flurbiprofen, ibuprofen, bromfenac, nepafenac, and ketorolac, salicylate, indomethacin, ibuprofen, naxopren, piroxicam and nabumetone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as antiallergenics, including, for example, sodium chromoglycate, antazoline, methapyriline, chlorpheniramine, cetrizine, pyrilamine, prophenpyridamine; anti-histamine agents such as azelastine, emedastine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor or antagonists thereof (such as those disclosed in U.S. Pat. No. 7,759,472 or U.S. patent application Ser. No. 12/465,051, 12/564,863, or 12/641,270, each of which is incorporated in its entirety by reference herein), transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers such as dorzolamide or betaxolol; compounds that promote blood oxygenation such as erythropoeitin; sodium channels blockers; calcium channel blockers such as nilvadipine or lomerizine; glutamate inhibitors such as memantine nitromemantine, riluzole, dextromethorphan or agmatine; acetylcholinsterase inhibitors such as galantamine; hydroxylamines or derivatives thereof, such as the water soluble hydroxylamine derivative OT-440; synaptic modulators such as hydrogen sulfide compounds containing flavonoid glycosides and/or terpenoids, such as *ginkgo biloba*; neurotrophic factors such as glial cell-line derived neutrophic factor, brain derived neurotrophic factor; cytokines of the IL-6 family of proteins such as ciliary neurotrophic factor or leukemia inhibitory factor; compounds or factors that affect nitric oxide levels, such as nitric oxide, nitroglycerin, or nitric oxide synthase inhibitors; cannabinoid receptor agonists such as WIN55-212-2; free radical scavengers such as methoxypolyethylene glycol thioester (MP-DTE) or methoxypolyethlene glycol thiol coupled with EDTA methyl triester (MPSEDE); anti-oxidants such as astaxathin, dithiolethione, vitamin E, or metallocorroles (e.g., iron, manganese or gallium corroles); compounds or factors involved in oxygen homeostasis such as neuroglobin or cytoglobin; inhibitors or factors that impact mitochondrial division or fission, such as Mdivi-1 (a selective inhibitor of dynamin related protein 1 (Drp1)); kinase inhibitors or modulators such as the Rho-kinase inhibitor H-1152 or the tyrosine kinase inhibitor AG1478; compounds or factors that affect integrin function, such as the Beta 1-integrin activating antibody HUTS-21; N-acyl-ethanaolamines and their precursors, N-acyl-ethanolamine phospholipids; stimulators of glucagon-like peptide 1 receptors (e.g., glucagon-like peptide 1); polyphenol containing compounds such as resveratrol; chelating compounds; apoptosis-related protease inhibitors; compounds that reduce new protein synthesis; radiotherapeutic agents; photodynamic therapy agents; gene therapy agents; genetic modulators; auto-immune modulators that prevent damage to nerves or portions of nerves (e.g., demyelination) such as glatimir; myelin inhibitors such as anti-NgR Blocking Protein, NgR(310)ecto-Fc; other immune modulators such as FK506 binding proteins (e.g., FKBP51); and dry eye medications such as cyclosporine A, delmulcents, and sodium hyaluronate.

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and. Valdecoxib; other immune-modulating agents such as aldesleukin, adalimumab (HUMIRA®), azathioprine, basiliximab, daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; anti-fungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-*mycobacterium* agents such as ethambutol, isoniazid, pyrazinamide, rifampin and rifabutin; anti-parasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or anti-herpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other anti-bacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombin inhibitors; antithrombogenic agents; anti-platelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

In some embodiments, the therapeutic agent is delivered through the implant to the desired location in the eye, such as the uveoscleral outflow pathway. In some embodiments, the therapeutic agent is delivered to the uveoscleral outflow pathway in combination with a therapeutic agent delivered via trans pars plana vitrectomy, thereby delivering a therapeutic agent to both sides of the retina. In some embodiments, the implant can improve access of topical medication to the posterior uvea. In some embodiments, the implant is used to delivery a topical medication to treat a chorio-retinal disease.

If desired, more than one implant of the same or different type may be implanted. For example, the implants disclosed herein may be used in combination with trabecular bypass shunts, such as those disclosed in U.S. Patent Publication 2004/0050392, and those described in U.S. Patent Publication 2005/0271704, filed Mar. 18, 2005, the entirety of which is incorporated herein by reference and made a part of this specification and disclosure. Additionally, implantation may be performed in combination with other surgical procedures, such as cataract surgery. All or a portion of the implant may be coated, e.g. with heparin, preferably in the flow path, to reduce blood thrombosis or tissue restenosis.

If desired, a multiplicity of implants having different flow capacities and/or lumen sizes may be implanted. For example, a single "large" lumen implant can be implanted first, and subsequent, depending on the pressure response to the first stent, a second can be added with potentially smaller flow capacity in order to "fine tune" the desired IOP. For example, the IOP of a first patient can safely be brought down to approximately 12-18 mm Hg, and once the flow capacity of the first stent is matched with the IOP reduction, a calculation can be made as to what additional outflow is required to achieve target pressures of, for example, approximately 8-12 mmHg. An appropriately sized implant can be added to accomplish the target pressure. Both implants can be proactively added at the same time based on calculated outflow requirements. Alternatively, the implants can be added sequentially as described above based on the measured effect of the first implant.

Kits

According to some embodiments, a kit (e.g., system or collection of items for a common purpose) for addressing ocular disorders is provided. The tem "kit" as used herein should be given its ordinary meaning and should include any system, grouping and/or collection of devices, systems, components, features, materials and/or the like provided for a common goal. In one embodiment, the kit comprises one or more of the following: a delivery apparatus (such as the multiple-implant delivery apparatus 200 described herein), a plurality of drainage implants (such as the drainage implants described herein), an incising member, and a sensor (such as a pressure sensor, an intraocular pressure sensor, an analyte sensor, a glucose sensor, or any other sensor configured for placement within an eye). In some embodiments, the drainage implants are pre-loaded within or on the delivery apparatus during manufacture and assembly prior to shipping. In other embodiments, the drainage implants are not pre-loaded. The kit can further comprise instructions for using the various devices, components and/or other features of the kit for a particular procedure or treatment protocol. For example, such instructions for use can include details regarding the order in which the devices, systems or other components are used, the duration of use and/or the like.

While certain embodiments of the disclosure have been described, these embodiments have been presented by way of example only, and are not intended to limit the scope of the disclosure. Indeed, the novel methods, systems, and devices described herein may be embodied in a variety of other forms. For example, embodiments of one illustrated or described implant can be combined with embodiments of another illustrated or described implant. Moreover, the implants described above can be utilized for other purposes. For example, the implants can be used to drain fluid from the anterior chamber to other locations of the eye or outside the eye. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Furthermore, various omissions, substitutions and changes in the form of the methods, systems, and devices described herein may be made without departing from the spirit of the disclosure.

Conditional language, for example, among others, "can," "could." "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

What is claimed is:

1. An implant delivery apparatus for treating an ocular disorder, comprising:
    at least two implants loaded within the implant delivery apparatus;
    a source of energy for selectively releasing energy to deliver said at least two implants into eye tissue;
    a cam operatively coupled to said source of energy and having a contoured profile configured to vary the amount of energy delivered to each implant during an implant delivery cycle;
    an implant advancement assembly comprising a collet and a cam follower operatively coupled to the cam such that said implant delivery cycle comprises retraction of the collet and advancement of the collet to effect implant delivery,
    wherein the contoured cam profile includes a first contoured cam profile portion corresponding to a first implant delivery cycle of a first implant of the at least two implants and a second contoured cam profile portion corresponding to a second implant delivery cycle of a second implant of the at least two implants, and wherein the second contoured cam profile is different than the first contoured cam profile.

2. The implant delivery apparatus of claim 1, wherein said source of energy comprises a source of stored energy.

3. The implant delivery apparatus of claim 1, wherein the implant delivery apparatus further comprises a retractable piercing member configured to create an incision in external eye tissue.

4. The implant delivery apparatus of claim 3, wherein the implant delivery apparatus further comprises a trocar configured to create at least two openings, for receiving a respective one of said implants within each opening, in internal eye tissue when said piercing member is retracted.

5. The implant delivery apparatus of claim 1, wherein each of said at least two implants comprises an inlet portion configured to be positioned in an anterior chamber of an eye and an outlet portion configured to be positioned in a physiologic outflow pathway of said eye.

6. The implant delivery apparatus of claim 1, wherein the implant delivery apparatus is disposable.

7. The implant delivery apparatus of claim 1, wherein the implant delivery apparatus comprises a safety mechanism that prevents reuse of the instrument.

8. The implant delivery apparatus of claim 7, wherein the safety mechanism comprises an internal component that renders the implant delivery apparatus inoperable if re-sterilized.

9. The implant delivery apparatus of claim 1, wherein said collet is connected to a holder that comprises the cam follower to engage said contoured profile of said cam.

10. The implant delivery apparatus of claim 9, wherein a spring biases said collet holder towards said cam.

11. An implant delivery apparatus for treating an ocular disorder, comprising:
    at least two implants loaded within the implant delivery apparatus;
    a source of energy for selectively releasing energy to deliver said at least two implants into eye tissue;

a cam operatively coupled to said source of energy and having a contoured profile about a circumference of the cam configured to vary the amount of energy delivered to each implant during an implant delivery cycle, wherein said cam is configured to rotate about a rotational pivot; and an implant advancement assembly comprising a collet and a cam follower that engages and follows the contoured profile of the cam such that said implant delivery cycle comprises retraction of the collet and advancement of the collet to effect implant delivery as the cam rotates, wherein the contoured cam profile includes a first contoured cam profile portion corresponding to a first implant delivery cycle of a first implant of the at least two implants and a second contoured cam profile portion corresponding to a second implant delivery cycle of a second implant of the at least two implants, and wherein the second contoured cam profile is different than the first contoured cam profile.

12. The implant delivery apparatus of claim 11, wherein said source of energy comprises a source of stored energy.

13. The implant delivery apparatus of claim 11, wherein the implant delivery apparatus further comprises a retractable piercing member configured to create an incision in external eye tissue.

14. The implant delivery apparatus of claim 13, wherein the implant delivery apparatus further comprises a trocar configured to create at least two openings, for receiving a respective one of said at least two implants within each opening, in internal eye tissue when said retractable piercing member is retracted.

15. The implant delivery apparatus of claim 11, wherein each of said at least two implants comprises an inlet portion configured to be positioned in an anterior chamber of an eye and an outlet portion configured to be positioned in a physiologic outflow pathway of said eye.

16. The implant delivery apparatus of claim 11, wherein the implant delivery apparatus is disposable.

17. The implant delivery apparatus of claim 11, wherein the implant delivery apparatus comprises a safety mechanism that prevents reuse of the implant delivery apparatus.

18. The implant delivery apparatus of claim 17, wherein the safety mechanism comprises an internal component that renders the implant delivery apparatus inoperable if re-sterilized.

19. The implant delivery apparatus of claim 11, wherein said collet is connected to a holder that comprises the cam follower to engage said contoured profile of said cam.

20. The implant delivery apparatus of claim 19, wherein a spring biases said collet holder towards said cam.

* * * * *